(12) United States Patent
Ullrich, Jr. et al.

(10) Patent No.: US 10,973,658 B2
(45) Date of Patent: Apr. 13, 2021

(54) ROTATING IMPLANT AND ASSOCIATED INSTRUMENTATION

(71) Applicant: Titan Spine, Inc., Mequon, WI (US)

(72) Inventors: Peter F. Ullrich, Jr., Neenah, WI (US); Kenneth Roggow, Milwaukee, WI (US); Pablo Polanco, Milwaukee, WI (US)

(73) Assignee: TITAN SPINE, INC., Mequon, WI (US)

( * ) Notice: Subject to any disclaimer, the term of this patent is extended or adjusted under 35 U.S.C. 154(b) by 167 days.

(21) Appl. No.: 16/195,516

(22) Filed: Nov. 19, 2018

(65) Prior Publication Data

US 2019/0192312 A1    Jun. 27, 2019

Related U.S. Application Data

(60) Provisional application No. 62/590,800, filed on Nov. 27, 2017.

(51) Int. Cl.
*A61F 2/46* (2006.01)
*A61F 2/44* (2006.01)
*A61F 2/30* (2006.01)

(52) U.S. Cl.
CPC ........ *A61F 2/4611* (2013.01); *A61F 2/30771* (2013.01); *A61F 2/447* (2013.01);
(Continued)

(58) Field of Classification Search
CPC .................................................... A61F 2/4611
See application file for complete search history.

(56) References Cited

U.S. PATENT DOCUMENTS 661,089 A    11/1900   Tanner
2,821,762 A   2/1958   Foose
(Continued)

FOREIGN PATENT DOCUMENTS

EP    2517676    10/2012
EP    2939639    4/2015
(Continued)

OTHER PUBLICATIONS

European Search Report dated Apr. 1, 2019 from the corresponding European application No. 18208411.
(Continued)

*Primary Examiner* — Andrew Yang
(74) *Attorney, Agent, or Firm* — Womble Bond Dickinson (US) LLP

(57) ABSTRACT

A system for use during surgical procedures. The system includes an implant and an inserter. The implant has a faceted post that rotates, ribs adapted to receive impact from an instrument to help position the implant, and stops. The inserter has a sleeve, into and from which a hook retracts and extends and on which a tab is disposed, and a pair of catches. The hook and tab combine to lock the post into position and to release the post so that the post can rotate. The engagements between the hook and the post and between the tab and the post permit rotation of the implant in situ. The stops and catches define an articulation range for the implant relative to a longitudinal axis of the inserter. A related method of using the system is also provided.

20 Claims, 13 Drawing Sheets

(52) U.S. Cl.
CPC .......... *A61F 2/4455* (2013.01); *A61F 2/4465* (2013.01); *A61F 2/4603* (2013.01); *A61F 2/4637* (2013.01); *A61F 2002/3054* (2013.01); *A61F 2002/3082* (2013.01); *A61F 2002/3093* (2013.01); *A61F 2002/30133* (2013.01); *A61F 2002/30331* (2013.01); *A61F 2002/30364* (2013.01); *A61F 2002/30365* (2013.01); *A61F 2002/30426* (2013.01); *A61F 2002/30476* (2013.01); *A61F 2002/30538* (2013.01); *A61F 2002/30593* (2013.01); *A61F 2002/30879* (2013.01); *A61F 2002/4615* (2013.01); *A61F 2002/4622* (2013.01); *A61F 2002/4628* (2013.01); *A61F 2002/4681* (2013.01)

(56) References Cited

U.S. PATENT DOCUMENTS

| | | | |
|---|---|---|---|
| 3,286,749 | A | 11/1966 | Learned |
| 3,995,371 | A | 12/1976 | O'Keefe |
| 4,060,114 | A | 11/1977 | Matsushima |
| 4,163,698 | A | 8/1979 | Kuo et al. |
| 4,865,303 | A | 9/1989 | Brantigan |
| 5,158,571 | A | 10/1992 | Picha |
| 5,391,422 | A | 2/1995 | Omori et al. |
| 5,443,514 | A | 8/1995 | Steffee |
| 6,436,102 | B1 | 8/2002 | Ralph et al. |
| 6,447,546 | B1 | 9/2002 | Bramlet et al. |
| 6,575,975 | B2 | 6/2003 | Brace et al. |
| 6,681,662 | B2 | 1/2004 | Blackston |
| 6,974,480 | B2 | 12/2005 | Messerli et al. |
| 6,981,975 | B2 | 1/2006 | Michelson |
| 7,056,321 | B2 | 6/2006 | Pagliuca et al. |
| 7,112,224 | B2 | 9/2006 | Liu et al. |
| 7,179,225 | B2 | 2/2007 | Shluzas et al. |
| D539,934 | S | 4/2007 | Blain |
| D541,940 | S | 5/2007 | Blain |
| 7,226,451 | B2 | 6/2007 | Shluzas et al. |
| D564,095 | S | 3/2008 | Blain |
| D566,276 | S | 4/2008 | Blain |
| 7,410,501 | B2 | 8/2008 | Michelson |
| 7,445,640 | B2 | 11/2008 | Despres, III et al. |
| D599,019 | S | 8/2009 | Pimenta et al. |
| 7,615,078 | B2 | 11/2009 | White et al. |
| 7,645,232 | B2 | 1/2010 | Shluzas |
| 7,651,496 | B2 | 1/2010 | Keegan et al. |
| 7,655,012 | B2 | 2/2010 | DiPoto et al. |
| 7,658,739 | B2 | 2/2010 | Shluzas |
| 7,662,190 | B2 | 2/2010 | Steinemann et al. |
| 7,691,120 | B2 | 4/2010 | Shluzas |
| 7,736,305 | B2 | 6/2010 | DiPoto |
| 7,744,612 | B2 | 6/2010 | Blain |
| 7,758,620 | B2 | 7/2010 | Porcher |
| 7,850,695 | B2 | 12/2010 | Pagliuca et al. |
| 7,976,464 | B2 | 7/2011 | Shluzas et al. |
| 7,998,172 | B2 | 8/2011 | Blain |
| 8,062,304 | B2 | 11/2011 | Blain et al. |
| 8,100,955 | B2 | 1/2012 | Blain et al. |
| 8,142,355 | B2 | 3/2012 | Blain et al. |
| 8,162,994 | B2 | 4/2012 | Gimbel et al. |
| 8,172,854 | B2 | 5/2012 | Blain et al. |
| 8,347,768 | B2 | 1/2013 | Witte |
| 8,353,913 | B2 | 1/2013 | Moskowitz et al. |
| 8,399,008 | B2 | 3/2013 | Webster et al. |
| 8,425,602 | B2 | 4/2013 | Guyer et al. |
| 8,523,930 | B2 | 9/2013 | Saunders et al. |
| 8,608,651 | B2 | 12/2013 | Shluzas |
| 8,702,762 | B2 | 4/2014 | Jacene et al. |
| 8,770,068 | B2 | 7/2014 | Witte |
| 8,864,785 | B2 | 10/2014 | Pagliuca et al. |
| 8,894,652 | B2 | 11/2014 | Seifert et al. |
| 8,979,749 | B2 | 3/2015 | Gorek et al. |
| 9,345,586 | B2 | 5/2016 | Hunt |
| 9,358,133 | B2 * | 6/2016 | Lindenmann ......... A61F 2/4465 |
| 2001/0001315 | A1 | 5/2001 | Bates et al. |
| 2001/0039464 | A1 | 11/2001 | Hackauf |
| 2002/0188294 | A1 | 12/2002 | Couture et al. |
| 2003/0031984 | A1 | 2/2003 | Rusin et al. |
| 2003/0189114 | A1 | 10/2003 | Taylor et al. |
| 2004/0041131 | A1 | 5/2004 | Krueger et al. |
| 2004/0098131 | A1 | 5/2004 | Bryan et al. |
| 2004/0117019 | A1 | 6/2004 | Trieu et al. |
| 2005/0101950 | A1 | 5/2005 | Fiere et al. |
| 2005/0131416 | A1 | 6/2005 | Jansen et al. |
| 2005/0251257 | A1 | 11/2005 | Michell et al. |
| 2005/0261768 | A1 | 11/2005 | Trieu |
| 2006/0004453 | A1 | 1/2006 | Bartish et al. |
| 2006/0041313 | A1 | 2/2006 | Allard et al. |
| 2006/0095136 | A1 | 5/2006 | McLuen |
| 2006/0116770 | A1 | 6/2006 | White et al. |
| 2006/0122701 | A1 | 6/2006 | Kiester |
| 2006/0121795 | A1 | 11/2006 | Bagga et al. |
| 2006/0265065 | A1 | 11/2006 | Bagga et al. |
| 2006/0287652 | A1 | 12/2006 | Lessig et al. |
| 2006/0293748 | A1 | 12/2006 | Alexander et al. |
| 2006/0293752 | A1 | 12/2006 | Moumene et al. |
| 2007/0062933 | A1 | 3/2007 | Weber |
| 2007/0093898 | A1 | 4/2007 | Schwab et al. |
| 2007/0118220 | A1 | 5/2007 | Liu et al. |
| 2007/0118223 | A1 | 5/2007 | Allard et al. |
| 2007/0118243 | A1 | 5/2007 | Schroeder et al. |
| 2007/0173938 | A1 | 7/2007 | Sweeney |
| 2007/0089905 | A1 | 8/2007 | Jackson et al. |
| 2007/0191958 | A1 | 8/2007 | Abdou |
| 2007/0213826 | A1 | 9/2007 | Smith et al. |
| 2007/0225808 | A1 | 9/2007 | Warnick |
| 2007/0233248 | A1 | 10/2007 | Schwab et al. |
| 2007/0255414 | A1 | 11/2007 | Melkent et al. |
| 2007/0260320 | A1 | 11/2007 | Peterman et al. |
| 2007/0269475 | A1 | 11/2007 | Gil et al. |
| 2007/0270951 | A1 | 11/2007 | Davis et al. |
| 2007/0270956 | A1 | 11/2007 | Heinz |
| 2007/0270960 | A1 | 11/2007 | Bonin et al. |
| 2007/0293949 | A1 | 12/2007 | Salerni et al. |
| 2008/0071380 | A1 | 3/2008 | Sweeney |
| 2008/0077171 | A1 | 3/2008 | Blain et al. |
| 2008/0119935 | A1 | 5/2008 | Alverez |
| 2008/0154378 | A1 | 6/2008 | Pelo |
| 2008/0249622 | A1 | 10/2008 | Gray |
| 2008/0269764 | A1 | 10/2008 | Blain et al. |
| 2008/0275459 | A1 | 11/2008 | Dickinson et al. |
| 2009/0005784 | A1 | 1/2009 | Blain et al. |
| 2009/0006225 | A1 | 1/2009 | Blain et al. |
| 2009/0014243 | A1 | 1/2009 | Whingham |
| 2009/0024132 | A1 | 1/2009 | Blain et al. |
| 2009/0054988 | A1 | 2/2009 | Hess |
| 2009/0029458 | A1 | 3/2009 | Lake et al. |
| 2009/0076613 | A1 | 3/2009 | Biedermann et al. |
| 2009/0076614 | A1 | 3/2009 | Arramon |
| 2009/0082819 | A1 | 3/2009 | Blain et al. |
| 2009/0204152 | A1 | 8/2009 | Blain |
| 2009/0259316 | A1 | 10/2009 | Ginn et al. |
| 2009/0265007 | A1 | 10/2009 | Colleran |
| 2009/0140544 | A1 | 11/2009 | Bertagnoli |
| 2010/0023057 | A1 | 1/2010 | Aeschlimann et al. |
| 2010/0057206 | A1 | 3/2010 | Duffield et al. |
| 2010/0121385 | A1 | 5/2010 | Blain et al. |
| 2010/0168798 | A1 | 7/2010 | Clineff et al. |
| 2010/0191337 | A1 * | 7/2010 | Zamani ................ A61F 2/4465 |
| | | | 623/17.16 |
| 2010/0274286 | A1 | 10/2010 | Blain et al. |
| 2010/0274358 | A1 | 10/2010 | Mueller et al. |
| 2011/0040301 | A1 | 2/2011 | Blain et al. |
| 2012/0078371 | A1 | 3/2012 | Gamache et al. |
| 2012/0095561 | A1 | 4/2012 | Voisard et al. |
| 2012/0123424 | A1 | 5/2012 | Blain et al. |
| 2012/0123548 | A1 | 5/2012 | Lynn et al. |
| 2012/0143341 | A1 | 6/2012 | Zipnick |
| 2012/0149991 | A1 | 6/2012 | Blain et al. |
| 2012/0158056 | A1 | 6/2012 | Blain |
| 2012/0232664 | A1 | 9/2012 | Ullrich, Jr. et al. |
| 2012/0239151 | A1 | 9/2012 | Ullrich, Jr. et al. |
| 2012/0282454 | A1 | 11/2012 | Jansen et al. |
| 2013/0150968 | A1 | 6/2013 | Dinville et al. |

(56) References Cited

U.S. PATENT DOCUMENTS

| | | |
|---|---|---|
| 2013/0245767 A1 | 9/2013 | Lee et al. |
| 2013/0268008 A1 | 10/2013 | McDonough et al. |
| 2014/0039626 A1 | 2/2014 | Mitchell |
| 2014/0309691 A1 | 10/2014 | Brown et al. |
| 2016/0052162 A1 | 2/2016 | Colin et al. |
| 2017/0091657 A1 | 6/2017 | Dee et al. |
| 2017/0172743 A1 | 6/2017 | Bonutti |
| 2017/0177046 A1 | 10/2017 | Behzadi |
| 2017/0290666 A1 | 10/2017 | Behzadi |
| 2017/0312084 A1 | 11/2017 | Ferro et al. |

FOREIGN PATENT DOCUMENTS

| | | |
|---|---|---|
| WO | 2001028469 | 4/2001 |
| WO | 2001095838 A1 | 12/2001 |
| WO | 2008103843 | 8/2008 |

OTHER PUBLICATIONS

Petrini, et al. "Biomedical Applications of Shape Memory Alloys", J. Metallurgy, vol. 2011, (2011)Article ID 501483 pp. 1-15.
Shellabear, M., et al., "DMLS-Development History and State of the Art", LANE Conference, 2004, Erlangen Germany.

\* cited by examiner

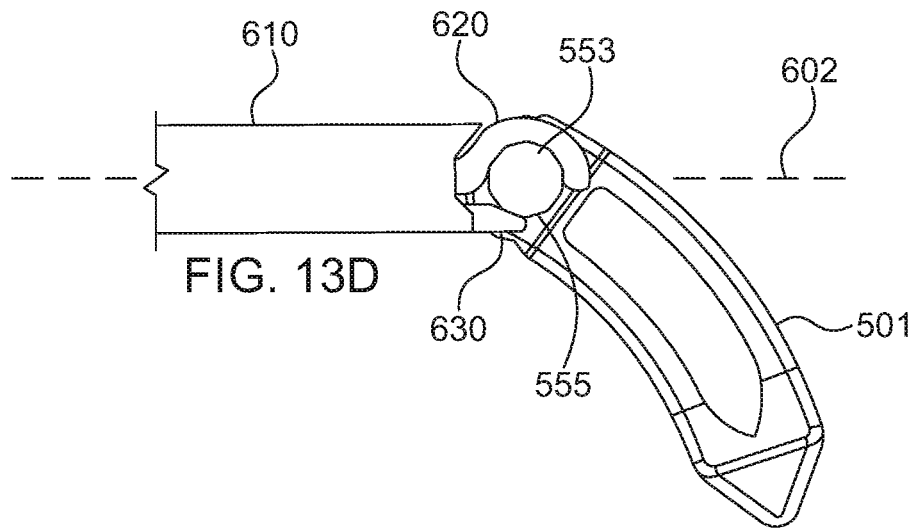
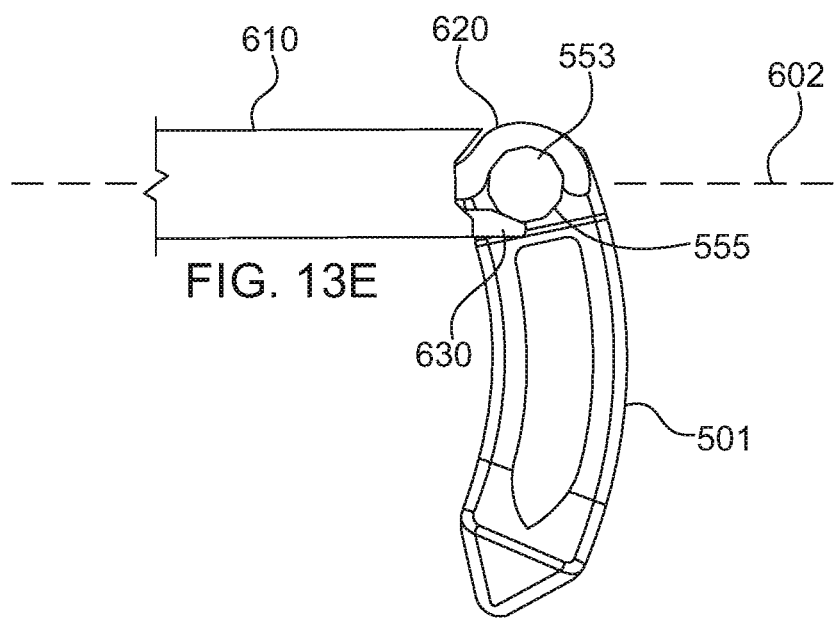

ROTATING IMPLANT AND ASSOCIATED INSTRUMENTATION

CROSS REFERENCE TO RELATED APPLICATIONS

This application claims priority to U.S. Patent Application No. 62/590,800 filed Nov. 27, 2017, the contents of which are incorporated by reference herein, in their entirety and for all purposes.

FIELD OF THE INVENTION

The invention relates generally to interbody spinal implants and, in particular, to a system including an implant and an instrument used during surgical procedures to manipulate and place the implant in a spine.

BACKGROUND OF THE INVENTION

In the simplest terms, the spine is a column made of vertebrae and discs. The vertebrae provide the support and structure of the spine while the spinal discs, located between the vertebrae, act as cushions or "shock absorbers." These discs also contribute to the flexibility and motion of the spinal column. Over time, the discs may become diseased or infected, develop deformities such as tears and cracks, or simply lose structural integrity, for example bulge or flatten. These impaired discs can affect the anatomical functions of the vertebrae, due to the resultant lack of proper biomechanical support, and are often associated with chronic back pain.

Several surgical techniques have been developed to address spinal defects, such as disc degeneration, deformity, or both. Spinal fusion has become a recognized surgical procedure for mitigating back pain by restoring biomechanical and anatomical integrity to the spine. Spinal fusion techniques involve the removal, or partial removal, of at least one intervertebral disc and preparation of the disc space for receiving an implant by shaping the exposed vertebral endplates. An implant is then inserted between the opposing endplates.

A spinal implant may be inserted during a spinal fixation procedure using an anterior, lateral, posterior, or transverse spinal approach. A discectomy may be performed to remove or partially remove a defective or damaged intervertebral disc. The discectomy may create a space for one or more spinal implants. The amount of removed disc material may correspond to the size and type of the spinal implant or spinal implants to be inserted.

Anterior interbody fusion procedures generally have reduced operative times, reduced blood loss, and do not interfere with the posterior anatomic structure of the lumbar spine. Anterior procedures also minimize scarring within the spinal canal while still achieving improved fusion rates, which is advantageous from a structural and biomechanical perspective. These generally preferred anterior procedures are particularly advantageous in providing improved access to the disc space, and thus correspondingly better endplate preparation.

Conventional transforaminal lateral interbody fusion (TLIF) implants are inserted using a combination of a linear insertion path and a hammering of the implant into the desired position using pushers that provide the desired anterior positioning of the implant. Alternatively, a stepwise straight hammering process alternating with an active turning technique is often used to manipulate the implant from the entry position to the final desired position. The conventional TLIF and other angular unilateral systems and insertion methods fail to provide implants, instrumentation, and methods that allow the implant to be easily inserted to its final desired position within the disc space—although many systems and methods have been suggested.

For example, U.S. Pat. No. 9,358,133 issued to Lindenmann et al. discloses a "Self-Pivoting Spinal Implant And Associated Instrumentation." The intervertebral implant includes an insertion end, an opposing engagement end, and first and second opposed main surfaces configured to contact respective adjacent vertebral endplates. Each of the first and second main surfaces has an anterior edge and a posterior edge, and extends between the insertion and engagement ends. Anterior and posterior walls are formed between the first and second main surfaces and along the respective anterior and posterior edges and converge at the insertion and engagement ends. A slot is formed at the engagement end and extends continuously between and at least partially along the anterior and posterior walls. A post is positioned within the slot, spaced from at least one of the anterior and posterior walls and extending at least partially between the first and second main surfaces. The post includes a plurality of exposed facets and is configured for engagement with a pivotable insertion instrument.

U.S. Pat. No. 9,345,586 issued to Hunt et al. discloses a "Variable Angle Spinal Surgery Instrument." Specifically, Hunt et al. teach an instrument for use in a procedure for inserting a spinal implant between human vertebrae. The instrument includes a shaft and an end member. The end member may rotate with respect to the shaft. An angle of the end member with respect to the shaft may be varied when the end member is in a disc space between the human vertebrae. The instrument may include a slide for securing the end member at selected angles relative to the shaft. The end member may be separable from the shaft when the end member is in a selected orientation with the shaft. An instrument kit may include a shaft assembly and modular end members for various steps in a surgical procedure, such as disc space preparation, disc space evaluation, and spinal implant insertion.

Spinal surgery is made complex, in part, by the proximity of the spinal cord, the cauda equina, or both. Preparation instruments and spinal implants may need to be carefully inserted to avoid damage to nerve tissue. Alignment and spacing of a spinal implant that is to be inserted into a patient may be determined before surgery. Achieving the predetermined alignment and spacing during surgery may be important to achieve optimal fusion of adjacent vertebrae.

More specifically, the unilateral transforaminal insertion of an interbody implant for lumbar spinal fusion presents challenges to the surgeon tasked with the procedure due to the curved manipulation path that the implant must undergo once it enters the disc space. The procedure presents a further challenge of coupling the implant to the inserter instrument while allowing the implant a limited amount of rotation or articulation to follow the desired path. These challenges also present themselves to other angular unilateral approaches to the spine, in which the initial access corridor is linear yet, once the implant enters the disc space, the implant must be manipulated or articulated along a curved path.

An implant system's corresponding surgical procedure, and the instruments used during such a procedure, should preserve as much vertebral endplate bone surface as possible by minimizing the amount of bone removed. This vertebral endplate bone surface, or subchondral bone, is generally much stronger than the underlying cancellous bone. Preservation of the endplate bone stock ensures biomechanical integrity of the endplates and minimizes the risk of implant subsidence. Thus, proper interbody implant design should provide for optimal seating of the implant while utilizing the maximum amount of available supporting vertebral bone stock.

Given the complexities of spinal surgery, a need exists for a spinal implant and associated instrument and method of use that improve the ease with which the implant may be manipulated during insertion or once within the disc space. Because safety, patient health, recovery speed, and reduced trauma are always surgical concerns, another need is to keep the insertion width required by the implant and instrument small. Another need is to allow the caretaker to manipulate the implant, using the instrument, within the disc space, in situ, without passing multiple instruments past the exposed nerve roots. A related need is to avoid or at least minimize the risk of trauma to the spine, as well as reduce the risk of damaging the nerve root with multiple passes of instrumentation.

SUMMARY OF THE INVENTION

To meet these and other needs, and in view of its purposes, the present invention provides a system for use during surgical procedures. The system includes an implant and an inserter. The implant has a faceted post that rotates, ribs adapted to receive impact from an instrument to help position the implant, and stops. The inserter has a sleeve, into and from which a hook retracts and extends and on which a tab is disposed, and a pair of catches. The hook and tab combine to lock the post into position and to release the post so that the post can rotate. The engagements between the hook and the post and between the tab and the post permit rotation of the implant in situ. The stops and catches define an articulation range for the implant relative to a longitudinal axis of the inserter.

A related method of using the system is also provided. The method follows, or may include the steps of, identification of a spinal disc in need of repair or replacement, performance of at least a partial discectomy to create a disc space, and selection of the appropriate size of implant for the disc space. The method includes the following steps. The caretaker couples the implant to the inserter by manipulating the actuator of the inserter to extend the hook away from the sleeve and, using the handle of the inserter, manipulating the sleeve so that the hook engages the post of the implant, and manipulating the actuator to retract the hook into the sleeve until the post of the implant engages the tab of the inserter, with full engagement between the hook and the post and between the tab and the post locking the post into the hook and the tab, preventing rotation of the post. The caretaker then grasps the handle of the inserter and inserts a tapered nose of the implant into the disc space created during the discectomy procedure until the tapered nose enters the disc space and begins to distract the adjacent vertebral bodies. Next, the caretaker optionally delivers impaction forces to one or both of a proximal end of the inserter and the ribs of the implant to urge the implant at least partially into the disc space. The caretaker then manipulates the inserter and the implant sequentially to engage, release the tab from the post of, rotate, and re-engage the tab with the post of the implant to guide the implant along a path to a desired final position within the disc space. The caretaker can then release the implant from the inserter by manipulating the handle and the actuator so that neither the hook nor the tab engage the post. Finally, the inserter is removed from the disc space.

It is to be understood that both the foregoing general description and the following detailed description are exemplary, but are not restrictive, of the invention.

BRIEF DESCRIPTION OF THE DRAWING

The invention is best understood from the following detailed description when read in connection with the accompanying drawing. It is emphasized that, according to common practice, the various features of the drawing are not to scale. On the contrary, the dimensions of the various features are arbitrarily expanded or reduced for clarity. Included in the drawing are the following figures:

FIGS. 13A, 13B, 13C, 13D, and 13E illustrate sequentially the various steps in the method by which the caretaker typically manipulates the system shown in FIG. 10 when the application is a TLIF surgical procedure;

DETAILED DESCRIPTION OF THE INVENTION

The invention relates to an implant and to an associated instrument used to manipulate and place the implant in a patient. The invention also relates to a system including both of the implant and the instrument as components. Certain embodiments of the invention may be especially suited for placement between adjacent human vertebral bodies. The implants of the invention may be used in procedures such as Anterior Lumbar Interbody Fusion (ALIF), Posterior Lumbar Interbody Fusion (PLIF), Transforaminal Lumbar Interbody Fusion (TLIF), and cervical fusion. Certain embodiments do not extend beyond the outer dimensions of the vertebral bodies.

The ability to achieve spinal fusion is directly related to the available vascular contact area over which fusion is desired, the quality and quantity of the fusion mass, and the stability of the interbody spinal implant. Interbody spinal implants, as now taught, allow for improved seating over the apophyseal rim of the vertebral body. Still further, interbody spinal implants, as now taught, better utilize this vital surface area over which fusion may occur and may better bear the considerable biomechanical loads presented through the spinal column with minimal interference with other anatomical or neurological spinal structures. Even further, interbody spinal implants, according to certain aspects of the invention, allow for improved visualization of implant seating and fusion assessment. Interbody spinal implants, as now taught, may also facilitate osteointegration with the surrounding living bone.

Anterior interbody spinal implants in accordance with certain aspects of the invention can be preferably made of a durable material such as stainless steel, stainless steel alloy, titanium, or titanium alloy, but can also be made of other durable materials such as, but not limited to, polymeric, ceramic, and composite materials. For example, certain embodiments of the invention may be comprised of a biocompatible, polymeric matrix reinforced with bioactive fillers, fibers, or both. Certain embodiments of the invention may be comprised of urethane dimethacrylate (DUDMA)/ tri-ethylene glycol dimethacrylate (TEDGMA) blended resin and a plurality of fillers and fibers including bioactive fillers and E-glass fibers. Durable materials may also consist of any number of pure metals, metal alloys, or both. Titanium and its alloys are generally preferred for certain embodiments of the invention due to their acceptable, and desirable, strength and biocompatibility. In this manner, certain embodiments of the present interbody spinal implant may have improved structural integrity and may better resist fracture during implantation by impact. Interbody spinal implants, as now taught, may therefore be used as a distractor or trial implant during implantation.

Figure 1:
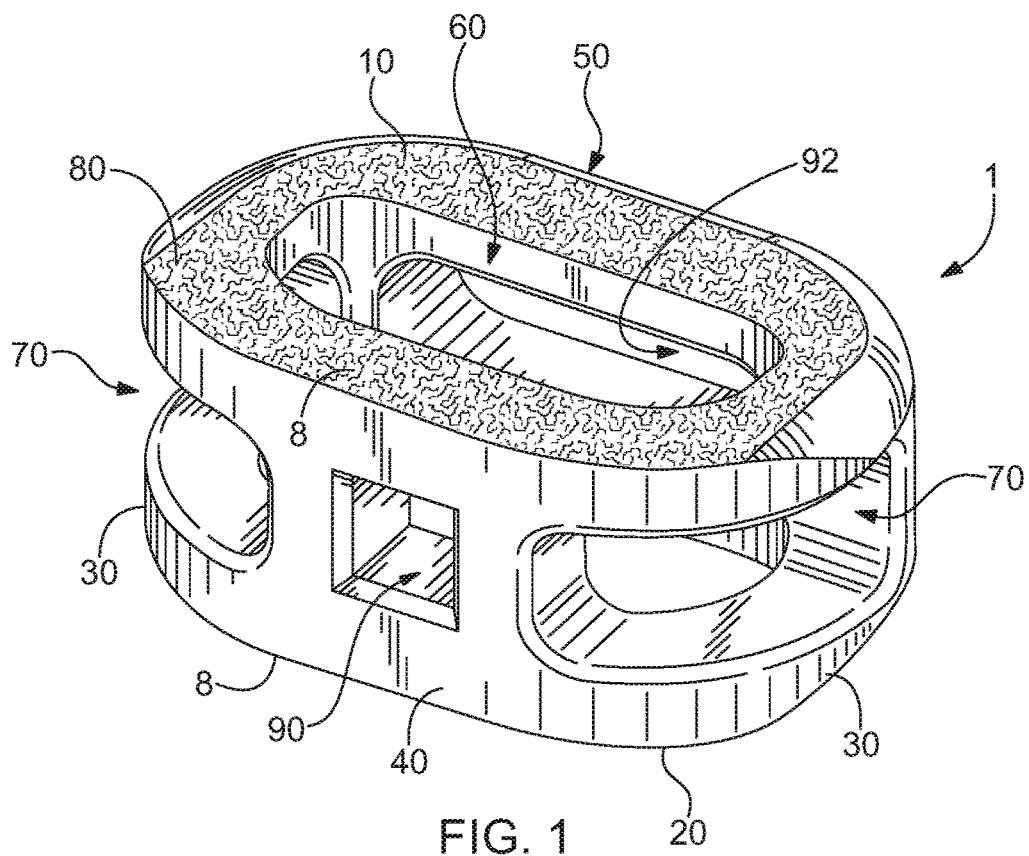
FIG. 1 shows a perspective view of an embodiment of the interbody spinal implant especially well adapted to be used in connection with an anterior lumbar interbody fusion (ALIF) surgical procedure.

Referring now to the drawing, in which like reference numbers refer to like elements throughout the various figures that comprise the drawing, FIG. 1 shows a perspective view of a first embodiment of the interbody spinal implant 1 especially well adapted for use in an ALIF procedure. The interbody spinal implant 1 includes a body having a top surface 10, a bottom surface 20, opposing lateral sides 30, and opposing anterior 40 and posterior 50 portions. One or both of the top surface 10 and the bottom surface 20 has a roughened topography 80. The roughened topography 80 is distinct, however, from the teeth provided on the surfaces of some conventional devices.

The implant 1 may include an anti-expulsion edge 8 at the junction between the top surface 10 and the anterior portion 40, at the junction between the bottom surface 20 and the anterior portion 40, or, as illustrated in FIG. 1, at both junctions. The anti-expulsion edge 8 helps to maintain the implant 1 in place, inhibiting migration and reducing the risk of undesired pull-out.

Figure 2:
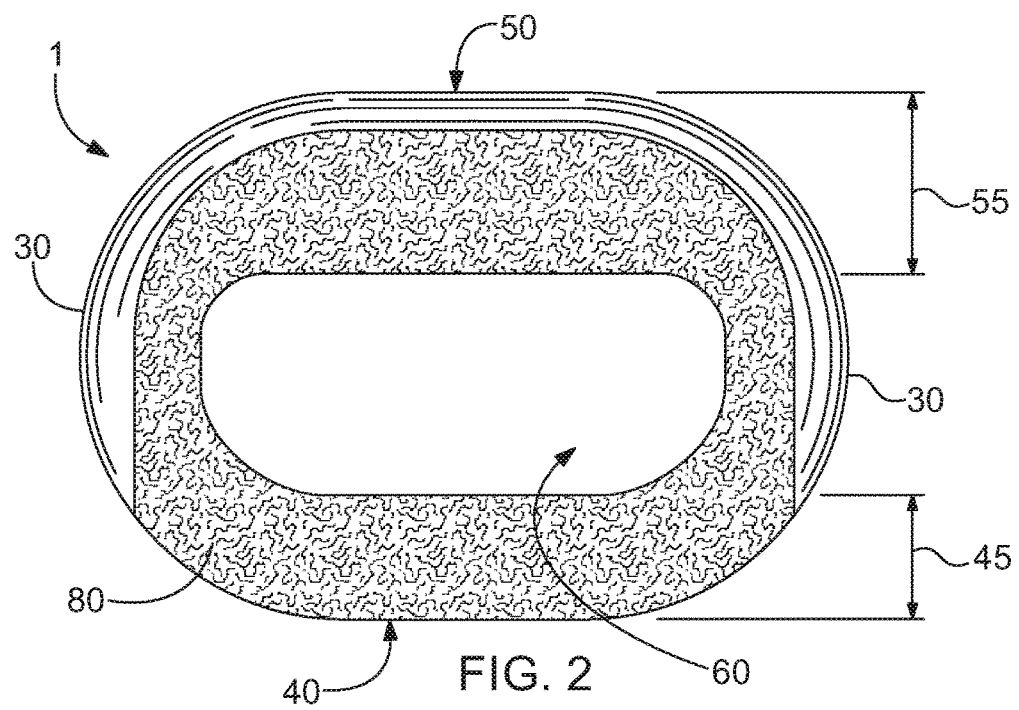
FIG. 2 shows a top view of the interbody spinal implant illustrated in FIG. 1.

In some aspects, the interbody spinal implant 1 is substantially hollow and has a generally oval-shaped transverse cross-sectional area with smooth, rounded, or both smooth and rounded lateral sides 30 and posterior-lateral corners. A substantially hollow implant 1 includes an implant 1 having at least about 33% of the interior volume of the implant 1 vacant. The implant 1 includes at least one vertical aperture 60 that extends the entire height of the implant body. As illustrated in the top view of FIG. 2, the vertical aperture 60 may further define a transverse rim 100 having a greater posterior portion thickness 55 than an anterior portion thickness 45.

In at least one embodiment, the opposing lateral sides 30 and the anterior portion 40 have an anterior portion thickness 45 of about 5 mm, while the posterior portion 50 has a posterior portion thickness 55 of about 7 mm. Thus, the posterior portion thickness 55 may allow for better stress sharing between the implant 1 and the adjacent vertebral endplates and helps to compensate for the weaker posterior endplate bone. In some aspects, the transverse rim 100 has a generally large surface area and contacts the vertebral endplate. The transverse rim 100 may act to better distribute contact stresses upon the implant 1, and hence minimize the risk of subsidence while maximizing contact with the apophyseal supportive bone. It is also possible for the transverse rim 100 to have a substantially constant thickness (e.g., for the anterior portion thickness 45 to be substantially the same as the posterior portion thickness 55) or for the posterior portion 50 to have a posterior portion thickness 55 less than that of the opposing lateral sides 30 and the anterior portion 40. Some studies have challenged the characterization of the posterior endplate bone as weaker.

The implant 1 may also have a lordotic angle to facilitate alignment. The anterior portion 40 is preferably generally greater in height than the posterior portion 50. Therefore, the implant 1 may better compensate for the generally less supportive bone found in certain regions of the vertebral endplate.

The implant 1 may further include at least one transverse aperture 70. Like the vertical aperture 60, the size and shape of the transverse aperture 70 are carefully chosen (and predetermined) to achieve a preferable design tradeoff for the particular application envisioned for the implant 1. (By "predetermined" is meant determined beforehand, so that the predetermined characteristic must be determined, i.e., chosen or at least known, in advance of some event—in this case before the manufacture of the implant 1.) Specifically, the transverse aperture 70 should have minimal dimensions to maximize the strength and structural integrity of the implant 1. On the other hand, the transverse aperture 70 should have maximum dimensions to (a) improve the visibility of the implant 1 during surgical procedures to ensure proper implant placement and seating, and to improve post-operative assessment of implant fusion, and (b) to facilitate engagement between bone graft material and adjacent bone. The substantially hollow area defined by the implant 1 may be filled with bone graft materials to facilitate the formation of a solid fusion column within the spine of a patient.

As illustrated in FIG. 1, the implant 1 has an opening 90 in the anterior portion 40. The opening 90 has a number of functions. One function is to facilitate manipulation of the implant 1 by the caretaker. Thus, the caretaker may insert a surgical tool into the opening 90 and, through the engagement between the surgical tool and the opening 90, manipulate the implant 1. The opening 90 may be threaded to enhance the engagement. A corresponding orifice 92 may be provided in the posterior portion 50. The opening 90 and orifice 92 facilitate both insertion of graft material into the interior of the implant 1 and improve visualization of the implant 1.

Figure 3:
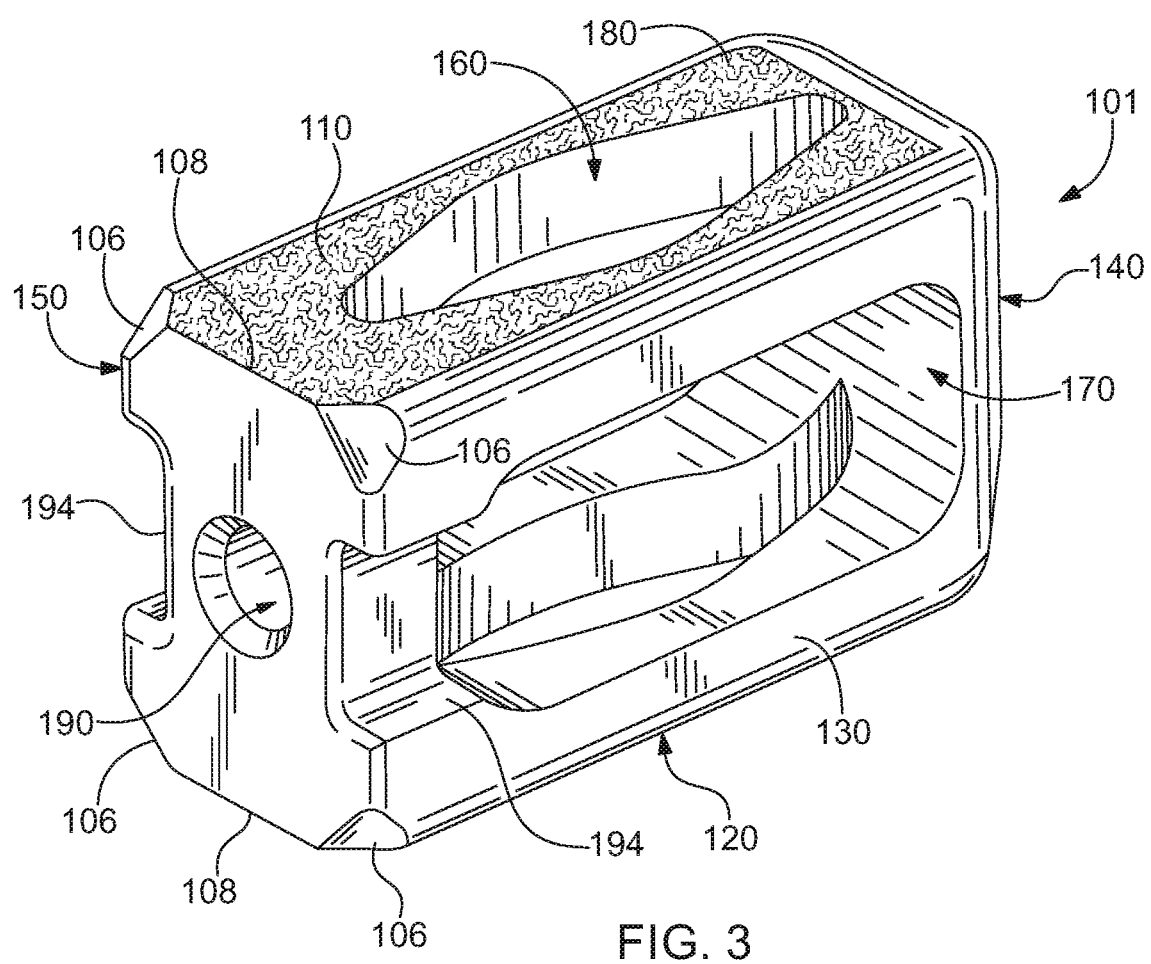
FIG. 3 shows a perspective view from the front of another embodiment of the interbody spinal implant especially well adapted to be used in connection with a posterior lumbar interbody fusion (PLIF) surgical procedure.
Figure 4:
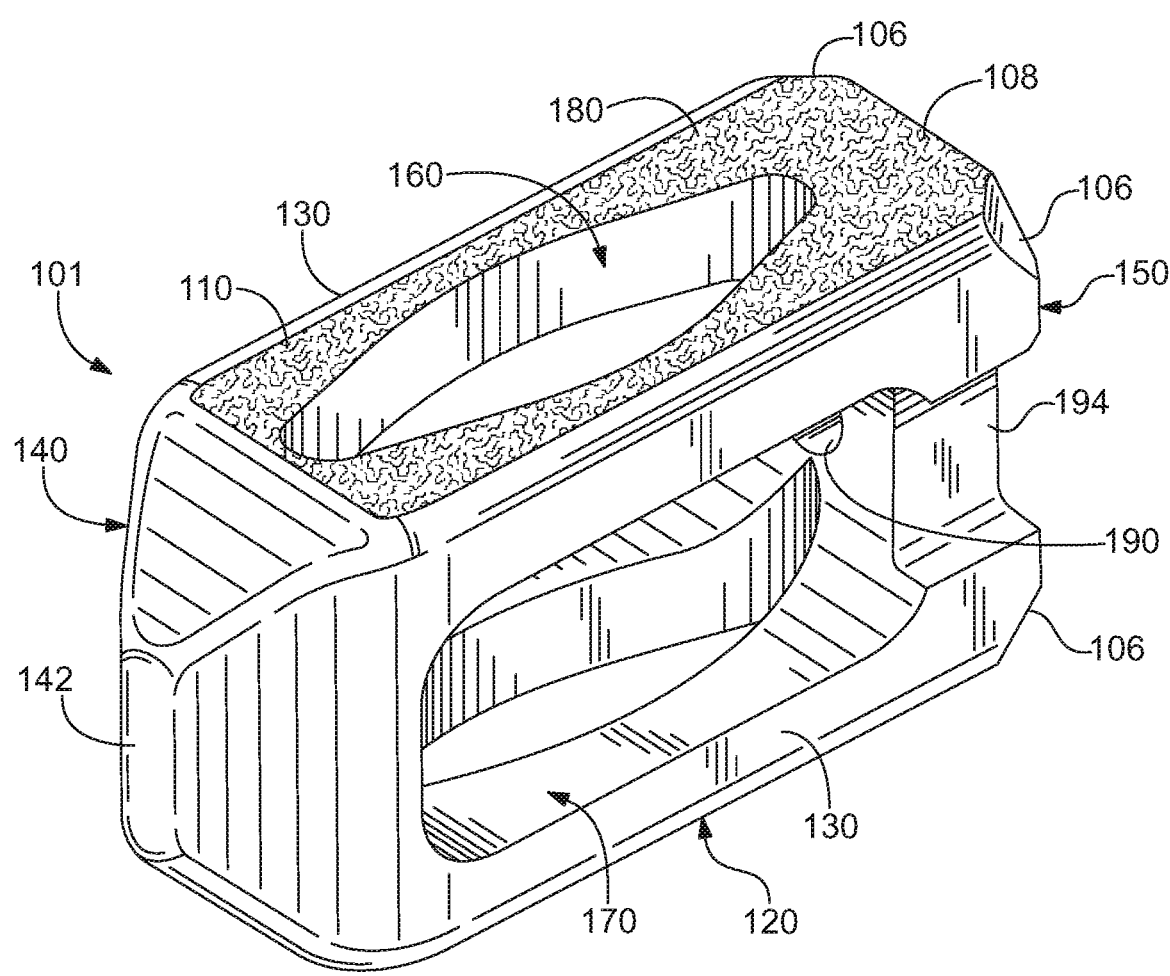
FIG. 4 shows a perspective view from the rear of the embodiment of the interbody spinal implant illustrated in FIG. 3.

As noted above, FIG. 1 shows a perspective view of one embodiment of the invention, the interbody spinal implant 1, which is especially well adapted for use in an ALIF procedure. Other embodiments of the invention are better suited for PLIF, TLIF, or cervical fusion procedures. Specifically, FIGS. 3 and 4 show perspective views of an embodiment of an interbody spinal implant 101 especially well adapted for use in a PLIF procedure. The interbody spinal implant 101 includes a body having a top surface 110, a bottom surface 120, opposing lateral sides 130, and opposing anterior 140 and posterior 150 portions. One or both of the top surface 110 and the bottom surface 120 has a roughened topography 180 for gripping adjacent bone and inhibiting migration of the implant 101.

Certain embodiments of the interbody spinal implant 101 are substantially hollow and have a generally rectangular shape with smooth, rounded, or both smooth and rounded lateral sides and anterior-lateral corners. As shown in FIG. 4, the anterior portion 140 may have a tapered nose 142 to facilitate insertion of the implant 101. To further facilitate insertion, the implant 101 has chamfers 106 at the corners of its posterior portion 150. The chamfers 106 prevent the implant 101 from catching upon insertion, risking potential damage such as severed nerves, while still permitting the implant 101 to have an anti-expulsion edge 108.

The implant 101 includes at least one vertical aperture 160 that extends the entire height of the implant body. The vertical aperture 160 further defines a transverse rim 200. The size and shape of the vertical aperture 160 are carefully chosen to achieve a preferable design tradeoff for the particular application envisioned for the implant 101. Specifically, the vertical aperture 160 seeks to maximize the surface area of the top surface 110 and the bottom surface 120 available proximate the anterior 140 and posterior 150 portions while maximizing both radiographic visualization and access to the bone graft material toward the center of the top 110 and bottom 120 surfaces. Thus, the size and shape of the vertical aperture 160 are predetermined by the application in which the implant 101 will be used.

In the particular example shown in FIGS. 3 and 4, the width of the implant 101 between the two lateral sides 130 is approximately 9 mm. The shape of the vertical aperture 160 approximates, in cross section, that of an American football. The center of the vertical aperture 160, which defines the maximum width of the vertical aperture 160, is about 5 mm. Thus, the thickness of the transverse rim 200 on either side of the vertical aperture 160 adjacent the center of the vertical aperture 160 is about 2 mm. These dimensions permit ample engagement between the bone graft material contained within the implant 101 and bone.

The vertical aperture 160 tapers from its center to its ends along a longitudinal distance of about 7.75 mm (thus, the total length of the vertical aperture 160 is about 15.5 mm). This shape leaves intact much of the transverse rim 200 in the areas around the ends of the vertical aperture 160. These areas may allow for better stress sharing between the implant 101 and the adjacent vertebral endplates. Thus, the transverse rim 200 has a generally large surface area and contacts the vertebral endplate.

As illustrated in FIG. 3, the implant 101 has an opening 190 in the posterior portion 150. The opening 190 has a number of functions. One function is to facilitate manipulation of the implant 101 by the caretaker. Thus, the caretaker may insert a surgical tool into the opening 190 and, through the engagement between the surgical tool and the opening 190, manipulate the implant 101. The opening 190 may be threaded to enhance the engagement.

The implant 101 may also have an Implant Holding Feature (IHF) 194 instead of or in addition to the opening 190. As illustrated in FIG. 3, the IHF 194 is located proximate the opening 190 in the posterior portion 150. In this particular example, the IHF 194 is a U-shaped notch. Like the opening 190, the IHF 194 has a number of functions, one of which is to facilitate manipulation of the implant 101 by the caretaker. Other functions of the opening 190 and the IHF 194 are to increase visibility of the implant 101 during surgical procedures and to enhance engagement between bone graft material and adjacent bone.

The implant 101 may further include at least one transverse aperture 170. Like the vertical aperture 160, the size and shape of the transverse aperture 170 are carefully chosen (and predetermined) to achieve a preferable design tradeoff for the particular application envisioned for the implant 101. Specifically, the transverse aperture 170 should have minimal dimensions to maximize the strength and structural integrity of the implant 101. On the other hand, the transverse aperture 170 should have maximum dimensions to (a) improve the visibility of the implant 101 during surgical procedures to ensure proper implant placement and seating, and to improve post-operative assessment of implant fusion, and (b) to facilitate engagement between bone graft material and adjacent bone. The substantially hollow area defined by the implant 101 may be filled with bone graft materials to facilitate the formation of a solid fusion column within the spine of a patient.

As shown in FIGS. 3 and 4, the transverse aperture 170 extends the entire transverse length of the implant body and nearly the entire height of the implant body. Thus, the size and shape of the transverse aperture 170 approach the maximum possible dimensions for the transverse aperture 170.

The section of the transverse aperture 170 proximate the IHF 194 is substantially rectangular in shape; the other section of the transverse aperture 170 has the shape of a curved arch. Other shapes and dimensions are suitable for the transverse aperture 170. In particular, all edges of the transverse aperture 170 may be rounded, smooth, or both.

The embodiment of the invention illustrated in FIGS. 3 and 4 is especially well suited for a PLIF surgical procedure. TLIF surgery is done through the posterior (rear) part of the spine and is essentially like an extended PLIF procedure. The TLIF procedure was developed in response to some of the technical problems encountered with a PLIF procedure. The main difference between the two spine fusion procedures is that the TLIF approach to the disc space is expanded by removing one entire facet joint; a PLIF procedure is usually done on both sides by only taking a portion of each of the paired facet joints.

By removing the entire facet joint, visualization into the disc space is improved and more disc material can be removed. Such removal should also provide for less nerve retraction. Because one entire facet is removed, the TLIF procedure is only done on one side: removing the facet joints on both sides of the spine would result in too much instability. With increased visualization and room for dissection, one or both of a larger implant and more bone graft can be used in the TLIF procedure. Theoretically, these advantages can allow the spine surgeon to distract the disc space more and realign the spine better (re-establish the normal lumbar lordosis).

Although the TLIF procedure offers some improvements over a PLIF procedure, the anterior approach in most cases still provides the best visualization, most surface area for healing, and the best reduction of any of the approaches to the disc space. These advantages must be weighed, however, against the increased morbidity (e.g., unwanted aftereffects and postoperative discomfort) of a second incision. Probably the biggest determinate in how the disc space is approached is the comfort level that the spine surgeon has with an anterior approach for the spine fusion surgery. Not all spine surgeons are comfortable with operating around the great vessels (aorta and vena cava) or have access to a skilled vascular surgeon to help them with the approach. Therefore, choosing one of the posterior approaches for the spine fusion surgery is often a more practical solution.

Figure 5:
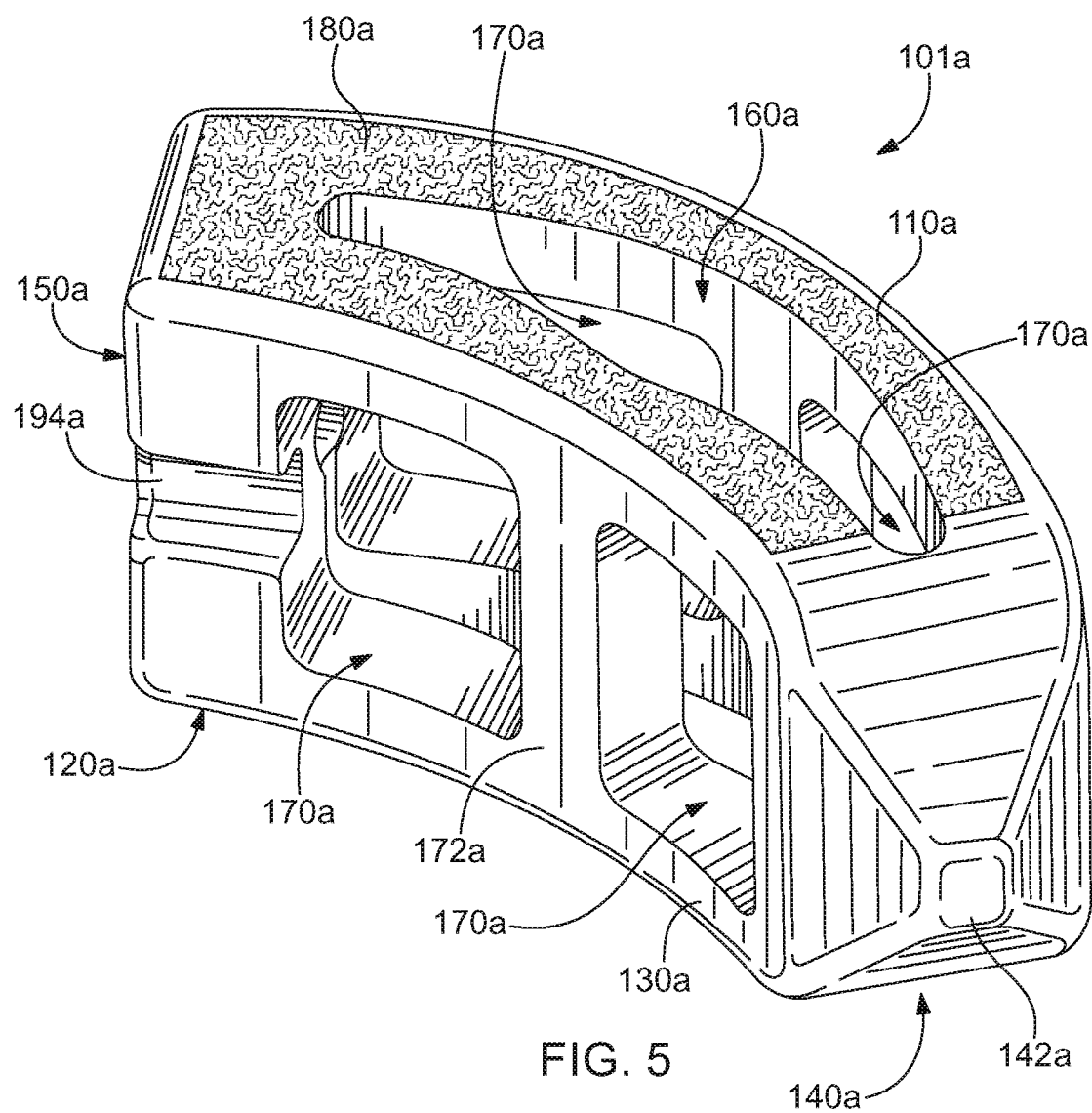
FIG. 5 shows a perspective view of another embodiment of the interbody spinal implant especially well adapted to be used in connection with a transforaminal lumbar interbody fusion (TLIF) surgical procedure.

The embodiment of the invention illustrated in FIG. 5 is especially well suited when the spine surgeon elects a TLIF procedure. Many of the features of the implant 101*a* illustrated in FIG. 5 are the same as those of the implant 101 illustrated in FIGS. 3 and 4. Therefore, these features are given the same reference numbers, with the addition of the letter "a," as those described with respect to the implant 101. The interbody spinal implant 101*a* includes a body having a top surface 110*a*, a bottom surface 120*a*, opposing lateral sides 130*a*, and opposing anterior 140*a* and posterior 150*a* portions. The anterior portion 140*a* may have a tapered nose 142*a* to facilitate insertion of the implant 101*a*. One or both of the top surface 110*a* and the bottom surface 120*a* has a roughened topography 180*a* for gripping adjacent bone and inhibiting migration of the implant 101*a*.

There are several differences, however, between the two embodiments (e.g., implant 101 and implant 101*a*). For example, unlike the substantially rectangular shape of the implant 101, the implant 101*a* has a curved shape. Further, the chamfers 106 and anti-expulsion edge 108 of the implant 101 are replaced by curves or rounded edges for the implant 101*a*. Still further, the TLIF procedure often permits use of a larger implant 101*a* which, in turn, may affect the size and shape of the predetermined vertical aperture 160*a*.

The substantially constant 9 mm width of the transverse rim 200 of the implant 101 is replaced with a larger, curved transverse rim 200*a*, The width of the transverse rim 200*a* is 9 mm in the regions adjacent the anterior 140*a* and posterior 150*a* portions. That width gradually increases to 11 mm, however, near the center of the transverse rim 200*a*. The additional real estate provided by the transverse rim 200*a* (relative to the transverse rim 200) allows the shape of the vertical aperture 160*a* to change, in cross section, from approximating a football to approximating a boomerang. Maintaining the thickness of the transverse rim 200*a* on either side of the vertical aperture 160*a* adjacent the center of the vertical aperture 160*a* at about 2 mm, similar to the dimensions of the implant 101, the center of the vertical aperture 160*a*, which defines the maximum width of the vertical aperture 160*a*, is increased (from 5 mm for the implant 101) to about 7 mm.

The implant 101*a* may also have a lordotic angle to facilitate alignment. The lateral side 130*a* depicted at the top of the implant 101*a* is preferably generally greater in height than the opposing lateral side 130*a*. Therefore, the implant 101*a* may better compensate for the generally less supportive bone found in certain regions of the vertebral endplate.

As shown in FIG. 5, the transverse aperture 170*a* extends the entire transverse length of the implant body and nearly the entire height of the implant body. FIG. 5 also highlights an alternative transverse aperture 170*a*, where the transverse aperture 170*a* is broken into two, separate sections by an intermediate wall 172*a*. Thus, the dimensions of the transverse aperture 170*a* shown in FIG. 5 are much smaller than those for a single transverse aperture 170*a*. The two sections of the alternative transverse aperture 170*a* are each illustrated as substantially rectangular in shape and extending nearly the entire height of the implant body; other sizes and shapes are possible for one or both sections of the alternative transverse aperture 170*a*.

The intermediate wall 172*a* may be made of the same material as the remainder of the implant 101*a* (e.g., metal), or it may be made of another material (e.g., PEEK) to form a composite implant 101*a*. It is also possible to extend the intermediate wall 172*a*, whether made of metal, PEEK, ultra-high molecular weight polyethylene (UHMWPE), or another material, to eliminate entirely the transverse aperture 170*a*. Given the reinforcement function of the intermediate wall 172*a*, the length of the vertical aperture 160*a* can be extended (as shown in FIG. 5) beyond the top surface 110*a* and into the anterior portion 140*a* of the implant 101*a*.

The embodiments of the invention described above are best suited for one or more of the ALIF, PLIF, and TLIF surgical procedures. Another embodiment of the invention is better suited for cervical fusion procedures. This embodiment is illustrated in FIGS. 6A and 6B as the interbody spinal implant 201.

Because there is not a lot of disc material between the vertebral bodies in the cervical spine, the discs are usually not very large. The space available for the nerves is also not that great, however, which means that even a small cervical disc herniation may impinge on the nerve and cause significant pain. There is also less mechanical load on the discs in the cervical spine as opposed to the load that exists lower in the spine. Among others, these differences have ramifications for the design of the implant 201.

The implant 201 is generally smaller in size than the other implant embodiments. In addition, the lower mechanical load requirements imposed by the cervical application typically render a composite implant unnecessary. Therefore, the implant 201 is generally made entirely of metal (e.g., titanium) and devoid of other materials (e.g., PEEK).

Figure 6A:
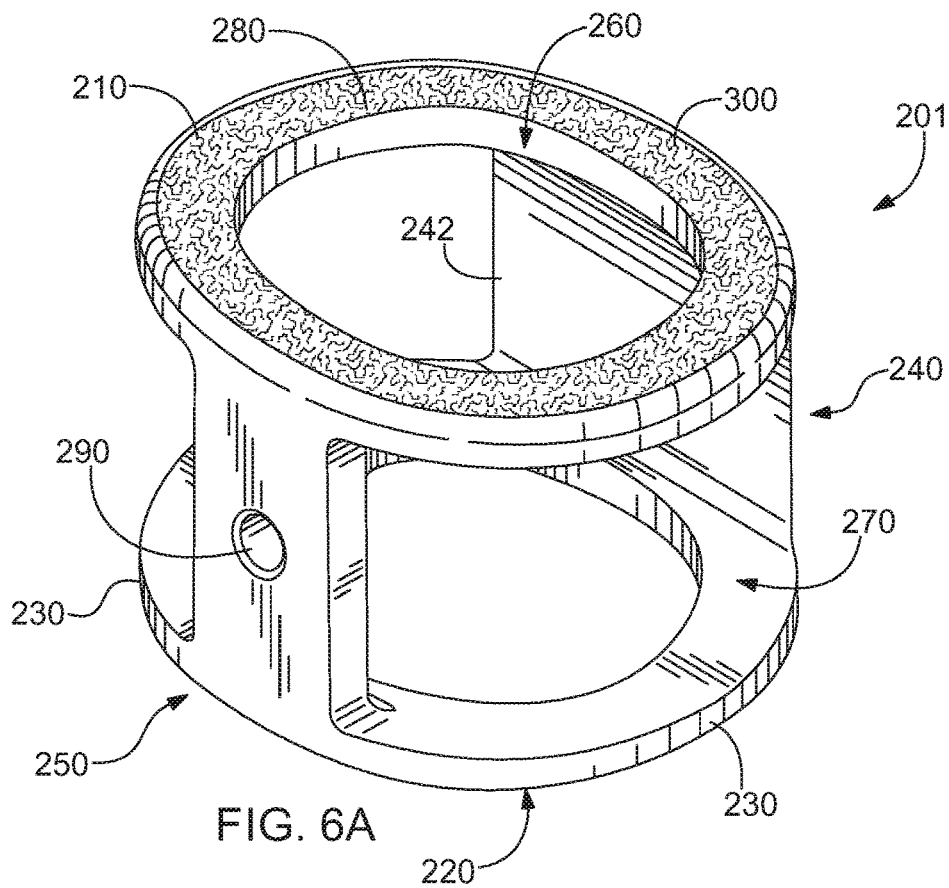
FIG. 6A shows a perspective view of another embodiment of the interbody spinal implant having a generally oval shape and being especially well adapted to be used in connection with a cervical spine surgical procedure.
Figure 6B:
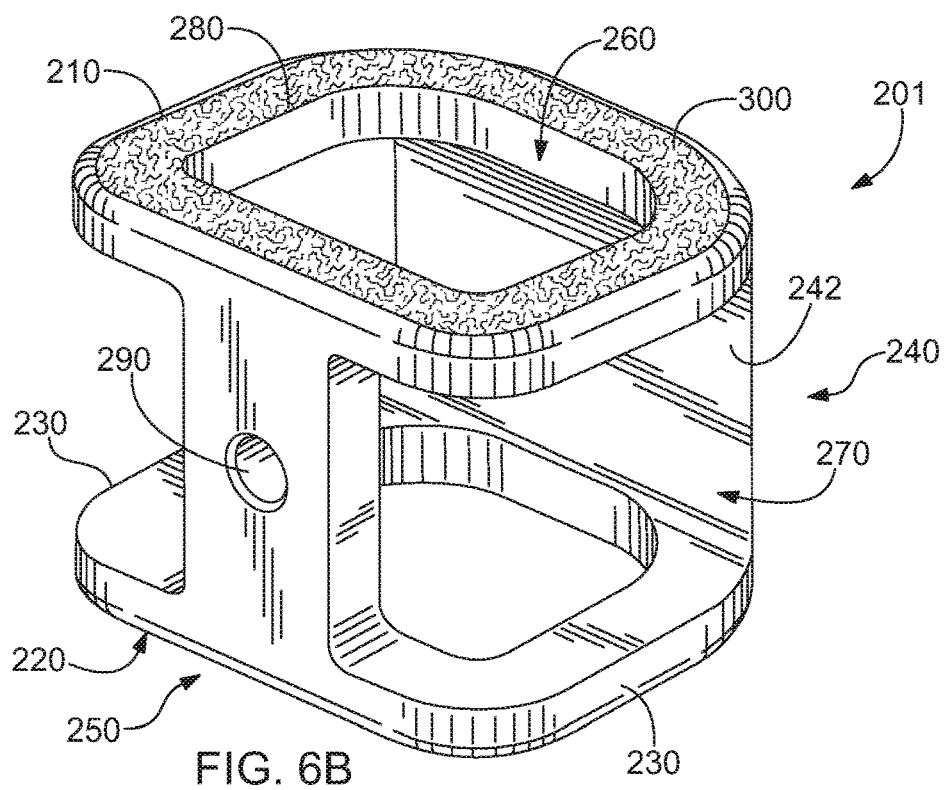
FIG. 6B shows a perspective view of a cervical implant having a generally box shape.

With specific reference to FIG. 6A and FIG. 6B, the implant 201 includes a body having a top surface 210, a bottom surface 220, opposing lateral sides 230, and opposing anterior 240 and posterior 250 portions. One or both of the top surface 210 and the bottom surface 220 has a roughened topography 280 for gripping adjacent bone and inhibiting migration of the implant 201. The implant 201 is substantially hollow and has a generally oval shape with smooth, rounded, or both smooth and rounded edges.

The implant 201 includes at least one vertical aperture 260 that extends the entire height of the implant body. The vertical aperture 260 further defines a transverse rim 300. The size and shape of the vertical aperture 260 are carefully chosen to achieve a preferable design tradeoff for the particular application envisioned for the implant 201. Specifically, the vertical aperture 260 seeks to maximize the surface area of the top surface 210 and the bottom surface 220, to allow for better stress sharing between the implant 201 and the adjacent vertebral endplates, while maximizing access to the bone graft material provided within the implant 201. Thus, the size and shape of the vertical aperture 260 are predetermined by the application.

As illustrated in FIG. 6A, the implant 201 has an opening 290 in the posterior portion 250. The opening 290 has a number of functions. One function is to facilitate manipulation of the implant 201 by the caretaker. Thus, the caretaker may insert a surgical tool into the opening 290 and, through the engagement between the surgical tool and the opening 290, manipulate the implant 201. The opening 290 may be threaded to enhance the engagement.

The implant 201 may further include at least one transverse aperture 270. Like the vertical aperture 260, the size and shape of the transverse aperture 270 are carefully chosen (and predetermined) to achieve a preferable design tradeoff for the particular application envisioned for the implant 201. For example, as shown in FIG. 6A, the transverse aperture 270 may extend the entire transverse length of the implant body and nearly the entire height of the implant body. Thus, the size and shape of the transverse aperture 270 approach the maximum possible dimensions for the transverse aperture 270.

As illustrated in FIG. 6A, the implant 201 may be provided with a solid rear wall 242. The rear wall 242 extends the entire width of the implant body and nearly the entire height of the implant body. Thus, the rear wall 242 essentially closes the anterior portion 240 of the implant 201. The rear wall 242 may offer one or more of several advantages, including reinforcement of the implant 201 and improved bone graft containment. In the cervical application, it may be important to prevent bone graft material from entering the spinal canal.

Alternative shapes for the implant 201 are possible. As illustrated in FIG. 6B, for example, the implant 201 may have a generally box shape which gives the implant 201 increased cortical bone coverage. Like the implant 201 shown in FIG. 6A, the implant 201 shown in FIG. 6B has a curved transverse rim 300 in the area of the anterior portion 240. The shape of the posterior portion 250 of the implant 201 is substantially flat, however, and the shape of the transverse rim 300 in the area of the posterior portion 250 is substantially square. Thus, the posterior portion 250 provides a face that can receive impact from a tool, such as a surgical hammer, to force the implant 201 into position.

The implant 201 may also have a lordotic angle to facilitate alignment. As illustrated in FIGS. 6A and 6B, the anterior portion 240 is preferably generally greater in height than the posterior portion 250. Therefore, the implant 201 may better compensate for the generally less supportive bone found in certain regions of the vertebral endplate. As an example, four degrees of lordosis may be built into the implant 201 to help restore balance to the spine.

Certain embodiments of the implant 1, 101, 101a, and 201 are generally shaped (i.e., made wide) to maximize contact with the apophyseal rim of the vertebral endplates. They are designed to be impacted between the endplates, with fixation to the endplates created by an interference fit and annular tension. Thus, the implants 1, 101, 101a, and 201 are shaped and sized to spare the vertebral endplates and leave intact the hoop stress of the endplates. A wide range of sizes are possible to capture the apophyseal rim, along with a broad width of the peripheral rim, especially in the posterior region. It is expected that such designs will lead to reduced subsidence. As much as seven degrees of lordosis (or more) may be built into the implants 1, 101, 101a, and 201 to help restore cervical balance.

When endplate-sparing spinal implant 1, 101, 101a, and 201 seats in the disc space against the apophyseal rim, it should still allow for deflection of the endplates like a diaphragm. This means that, regardless of the stiffness of the spinal implant 1, 101, 101a, and 201, the bone graft material inside the spinal implant 1, 101, 101a, and 201 receives load, leading to healthy fusion. The vertical load in the human spine is transferred though the peripheral cortex of the vertebral bodies. By implanting an apophyseal-supporting inter-body implant 1, 101, 101a, and 201, the natural biomechanics may be better preserved than for conventional devices.

Figure 7:
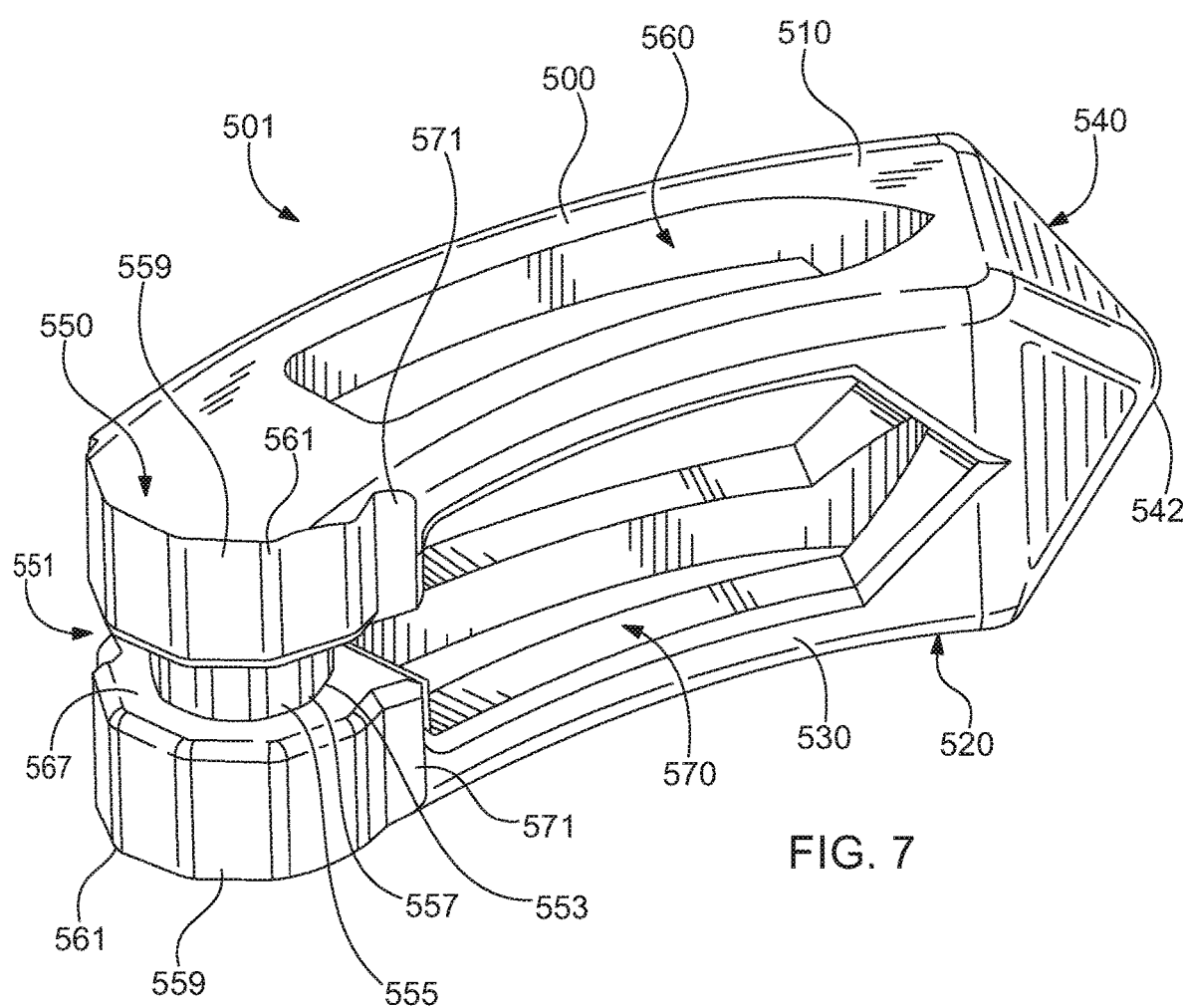
FIG. 7 shows a perspective view of another embodiment of the interbody spinal implant especially well adapted to be used in connection with a TLIF surgical procedure and having an inserter engagement portion according to the invention.

Like the embodiment of the implant 101a illustrated in FIG. 5, the embodiment of the implant 501 illustrated in FIGS. 7 (a perspective view), 8 (a top view), and 9 (a side view) is especially well suited for a TLIF surgical procedure. The primary distinction between the two TLIF implant embodiments is that the implant holding feature 194a of the implant 101a has been replaced by an inserter engagement portion 551 located at the posterior portion 550 of the implant 501. Otherwise, the implant 501 has substantially the same design as the implant 101a.

Figure 8:
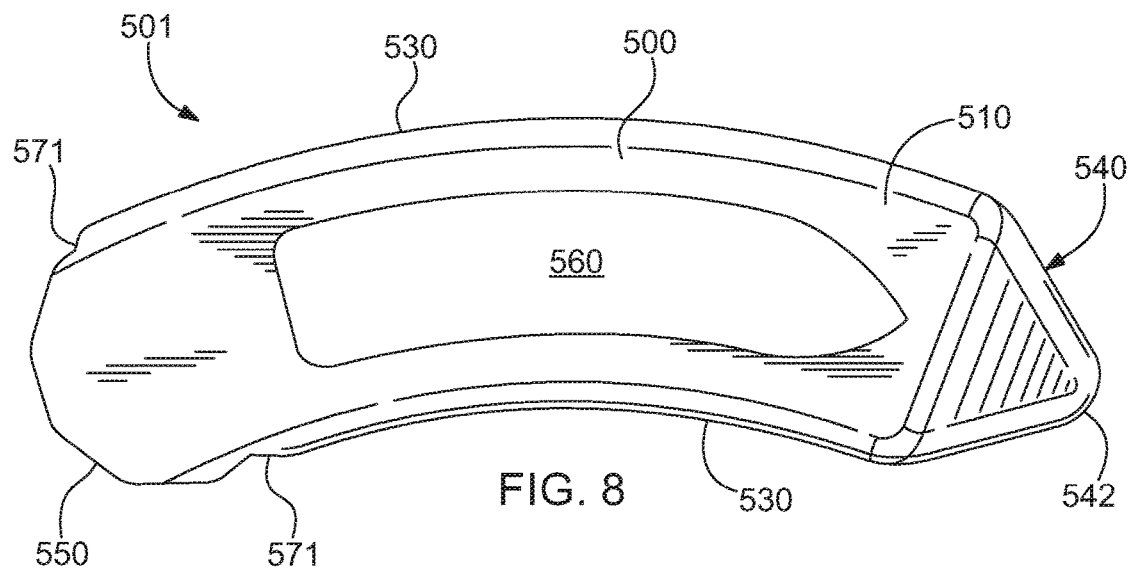
FIG. 8 shows a top view of the interbody spinal implant illustrated in FIG. 7.
Figure 9:
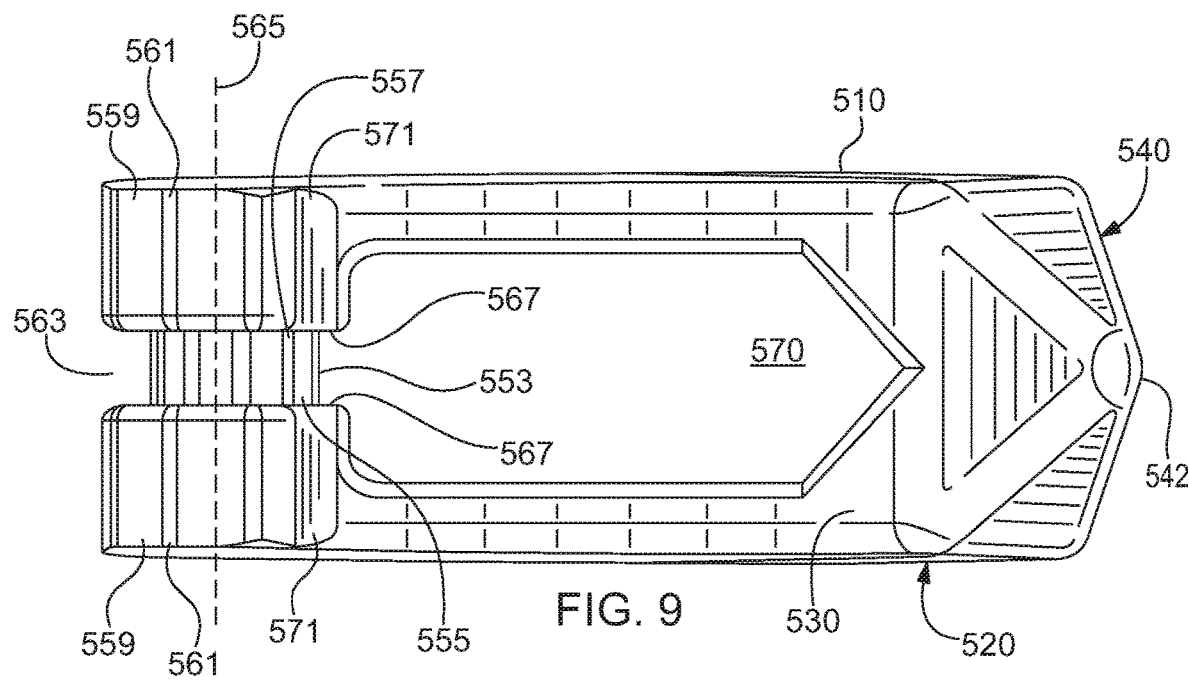
FIG. 9 shows a side view of the interbody spinal implant illustrated in FIGS. 7 and 8.

More specifically, the interbody spinal implant 501 includes a body having a top surface 510, a bottom surface 520, opposing lateral sides 530, and opposing anterior 540 and posterior 550 portions. The implant 501 includes at least one vertical aperture 560 that extends the entire height of the implant body and at least one transverse aperture 570 that extends the entire transverse length of the implant body and nearly the entire height of the implant body. As illustrated in the top view of FIG. 8, the vertical aperture 560 may further define a transverse rim 500. The anterior portion 540 may have a tapered nose 542 to facilitate insertion of the implant 501.

The implant 501 may also have a lordotic angle to facilitate alignment. The lateral side 530 depicted at the top of the implant 501 is preferably generally greater in height than the opposing lateral side 530. Therefore, the implant 501 may better compensate for the generally less supportive bone found in certain regions of the vertebral endplate.

One or more of the features illustrated and described above for the embodiments of the implant 1, 101, 101a, and 201 can be incorporated into the implant 501. Such features include, without limitation, the edge 8, 108; the roughened topography 80, 180, 180a, and 280; and the rear wall 242. On the other hand, the inserter engagement portion 551 depicted on the implant 501 can be incorporated into any one of the other embodiments of the implant 1, 101, 101a, and 201.

Turning to the inserter engagement portion 551, the inserter engagement portion 551 has several components. As illustrated on the implant 501, the inserter engagement portion 551 has a post 553 extending vertically between the top surface 510 and the bottom surface 520 of the implant 501. The post 553 is located and recessed within a slot 563 created in the posterior portion 550 of the implant 501. The slot 563 forms a step 567 in the body of the implant 501 at the posterior portion 550.

The post 553 is free to rotate within the slot 563 about a vertical axis 565 and relative to the body of the implant 501. A plurality of facets 555 are formed in the surface of the post 553, with the facets 555 separated by a series of partitions 557. Each of the facets 555 and the partitions 557 has a flat surface; the junctions between the facets 555 and partitions 557 are angled yielding a nut-like design. Although any number of facets 555 and partitions 557 are possible, the facets 555 and partitions 557 may give the surface of the post 553 a polygonal (and, preferably, an octagonal) shape.

The inserter engagement portion 551 has, as another component, a plurality of ribs 559 separated by a series of columns 561 on the posterior portion 550 of the implant 501. The ribs 559 and the columns 561 extend both from the top surface 510 to the top of the step 567 formed by the slot 563 and from the bottom surface 520 to the bottom of the step 567 formed by the slot 563. Each of the ribs 559 and the columns 561 has a flat surface; the junctions between the ribs 559 and columns 561 are angled yielding a nut-like design. The flat faces of the ribs 559 are adapted to receive impact (force) from a hammer or other instrument typically used by a caretaker to help position the implant 501 between vertebrae. Although any number of ribs 559 and columns 561 are possible, six ribs 559 separated by five columns 561 are suitable.

The inserter engagement portion 551 has, as yet another component, a number of stops 571 on the posterior portion 550 of the implant 501. The stops 571 prevent the caretaker from over-rotating the implant 501 about the vertical axis 565 and, therefore, function as a safety feature. Each of the stops 571 has a flat surface. Although any number of stops 571 are possible, four stops 571 are suitable.

Figure 10:
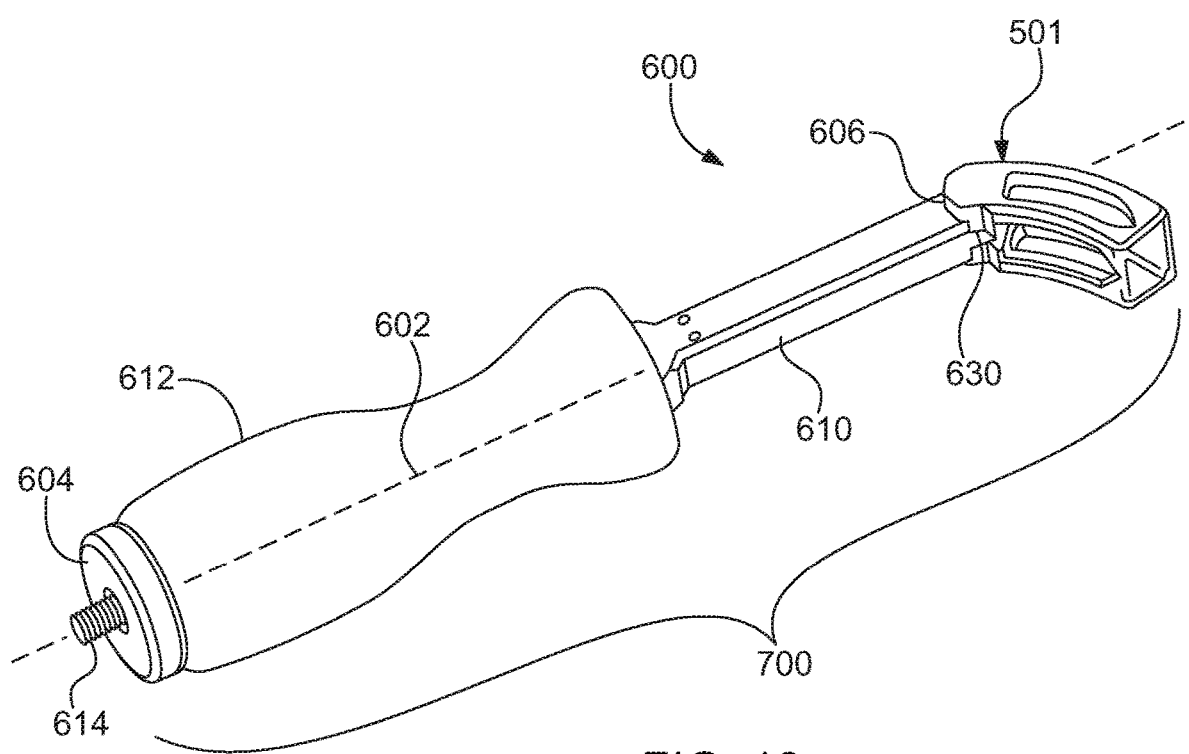
FIG. 10 shows an exemplary embodiment of the inserter that, together with the implant, form the components of the system according to the present invention.

To facilitate manipulation and placement of the implant 501 by the caretaker, an inserter 600 is provided. As illustrated in FIG. 10, the inserter 600 has a longitudinal axis 602 extending between a proximal end 604 and a distal end 606. The terms "distal" and "distal end" are used to define the part or surface of a component which is facing the patient or positioned furthest from the user. The terms "proximal" and "proximal end" are used to define the part or surface of a component which is facing away from the patient or positioned closest to the user.

The inserter 600 includes an elongated outer sleeve 610 that surrounds an elongated inner hook 620. The hook 620 is configured to be translatable with respect to the sleeve 610 along the longitudinal axis 602. More specifically, the hook 620 slides within the sleeve 610. Thus, the hook 620 can both be extended from and be retracted into the sleeve 610 by actions of the user.

The proximal end 604 of the sleeve 610 includes a handle 612 and an actuator 614. The caretaker can grasp the handle 612 comfortably and easily in the hand to hold and manipulate the inserter 600 and, ultimately, the implant 501. Thus, as illustrated in FIG. 10, the system 700 has two components: the implant 501 and the inserter 600. The caretaker can use the actuator 614 to translate the hook 620 with respect to the sleeve 610.

The distal end of the sleeve 610 includes a tab 630 affixed to and extending outward from the sleeve 610 along the longitudinal axis 602 and parallel to the hook 620. Preferably, the tab 630 is integral with the sleeve 610. By "integral" is meant a single piece or a single unitary part that is complete by itself without additional pieces, i.e., the part is of one monolithic piece formed as a unit with another part. The hook 620 and the tab 630 are separated by a gap 625 (highlighted in FIGS. 11A and 11B).

Figure 11A:
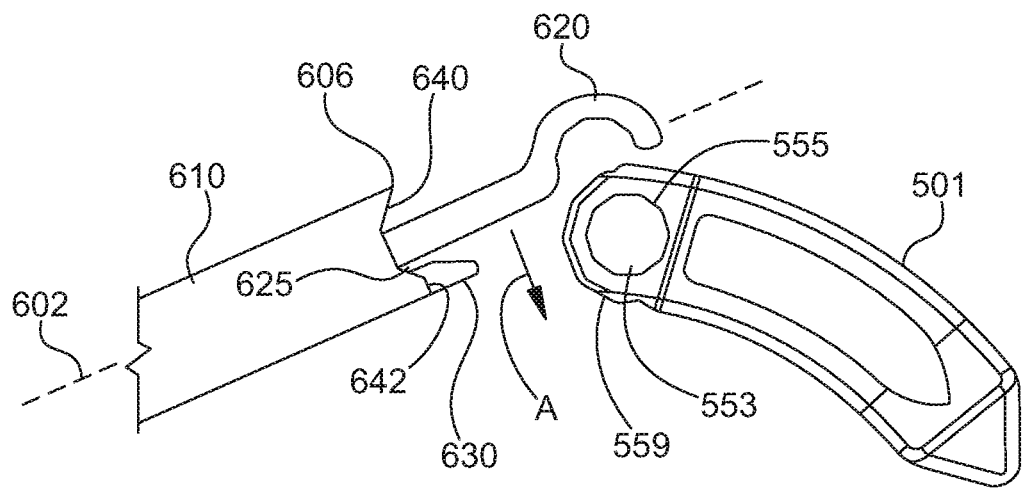
FIGS. 11A, 11B, and 11C illustrate sequentially the three, general steps by which the inserter shown in FIG. 10 engages the implant according to an embodiment of the present invention.
Figure 11B:
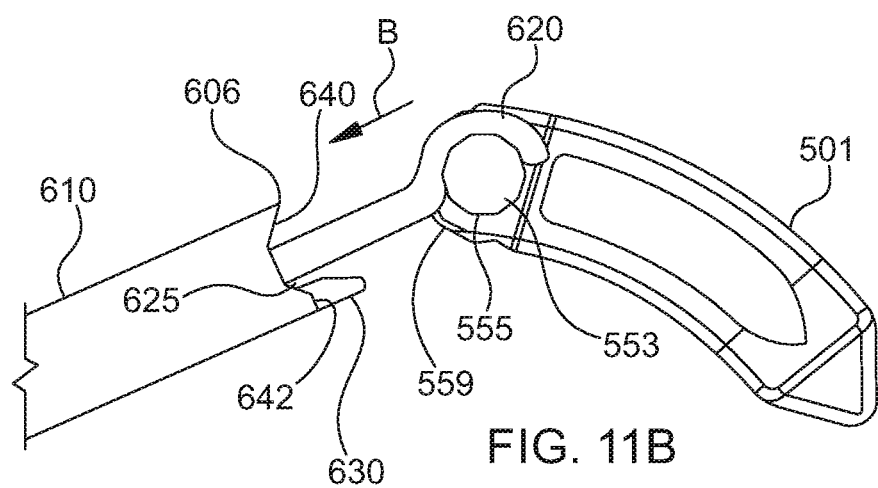
Figure 11C:
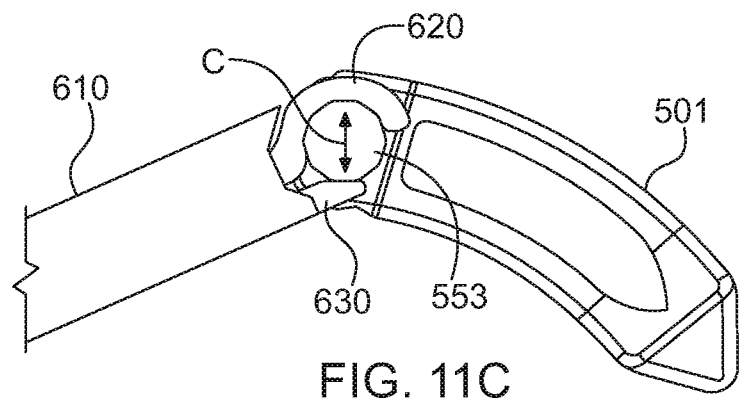

FIGS. 11A, 11B, and 11C illustrate the three, general steps by which the inserter 600 engages the implant 501. More specifically, the hook 620 and tab 630 of the inserter 600 engage the post 553 of the inserter engagement portion 551 of the implant 501. In the first step of engagement illustrated in FIG. 11A, the caretaker manipulates the actuator 614 to extend the hook 620 away from the sleeve 610 and, using the handle 612, manipulates the sleeve 610 so that the hook 620 moves in the direction of arrow A toward the post 553 of the implant 501. The hook 620 will enter the slot 563, guided by the step 567, and contact the facets 555 on the post 553. The inner surface of the hook 620 is shaped to correspond geometrically with the facets 555 so that, when the hook 620 fully engages the post 553, the inner surface of the hook 620 contacts each of a plurality of the facets 555 on the post 553. As illustrated in FIGS. 11B and 11C, the hook 620 typically contacts somewhat more than 50% of the facets 555 (although more or less contact may be suitable for a given application).

In the second step of engagement illustrated in FIG. 11B, the caretaker manipulates the actuator 614 to retract the hook 620 into the sleeve 610 in the direction of arrow B. Retraction continues until the post 553 of the implant 501 engages the tab 630 of the inserter 610—as illustrated in FIG. 11C. The inner surface of the tab 630 is shaped to correspond geometrically with at least one the facets 555 so that, when the tab 630 fully engages the post 553, the inner surface of the tab 630 contacts fully at least one of the facets 555 on the post 553. FIG. 11C illustrates the hook 620 and tab 630 fully engaged with the post 553. Arrow C highlights the opposing contact or engagement points between (i) the hook 620 and the post 553, and (ii) the tab 630 and the post 553. Such full engagement locks the post 553 into the geometry of the hook 620 and the corresponding geometry of the tab 630, preventing rotation of the post 553.

Figure 12:
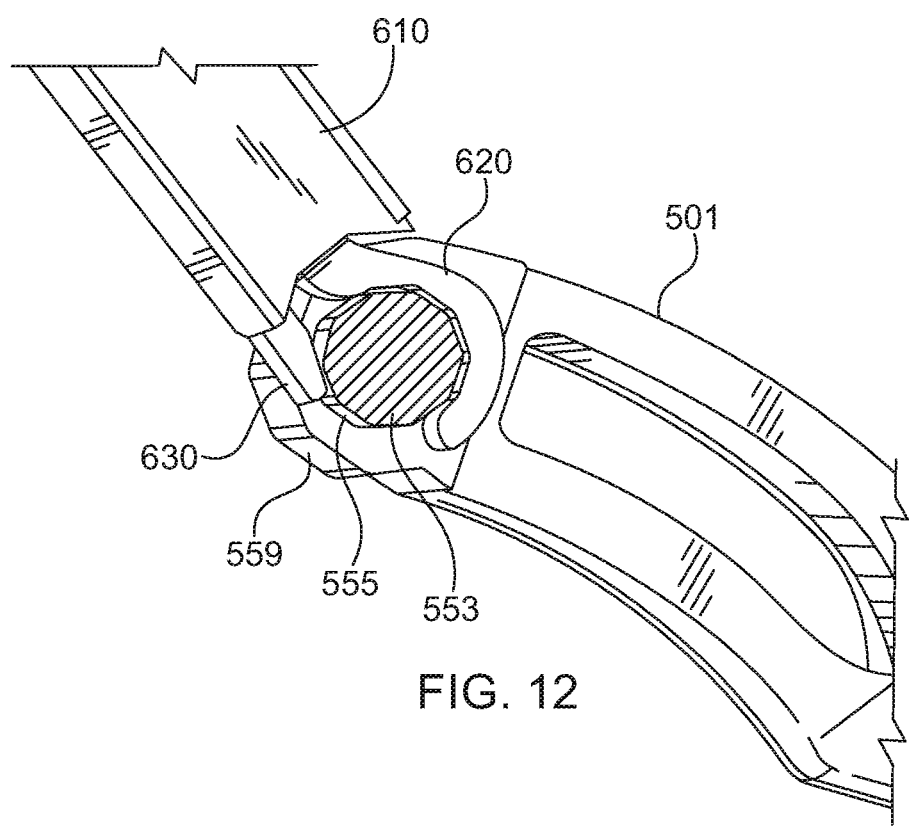
FIG. 12 illustrates full, locking engagement between the post of the implant and the hook and the tab of the inserter according to an embodiment of the present invention.

Like FIG. 11C, FIG. 12 illustrates full, locking engagement between the post 553 of the implant 501 and the hook 620 and the tab 630 of the inserter 600. A comparison between the relative positions of the implant 501 and the inserter 600 illustrated in FIGS. 11C and 12 advises, however, that the locked position can orient the two components of the system 700 (namely, the implant 501 and the inserter 600) in a variety of positions. The locked position allows the caretaker to push robustly on the post 553, perhaps using a separate instrument such as an impactor or hammer, and manipulate the implant 501 in situ (i.e., with the disk space).

FIGS. 11A, 11B, and 11C also illustrate a first catch 640 and a second catch 642 located on the sleeve 610 at the distal end 606. More specifically, the first catch 640 is located proximate the hook 620; the second catch 642 is located proximate the tab 630. Each of the first catch 640 and the second catch 642 can be formed by a linear taper angled away from the longitudinal axis 602 of the sleeve 610.

Figure 13A:
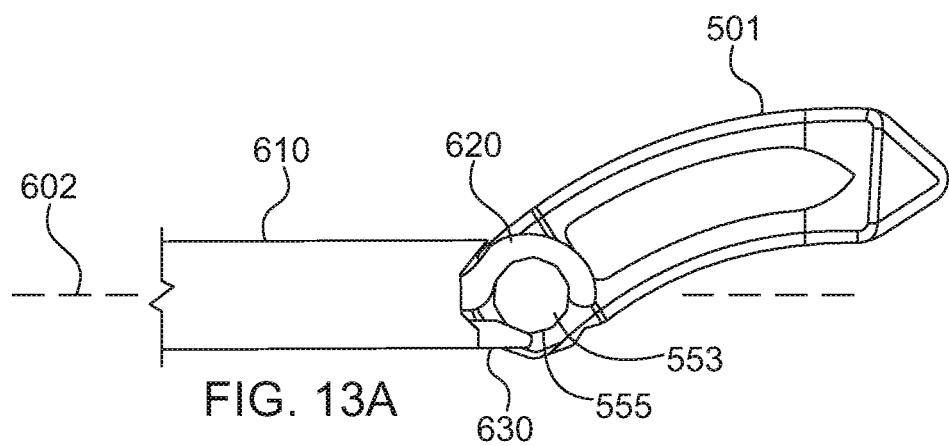

FIGS. 13A, 13B, 13C, 13D, and 13E illustrate the various steps in the method by which the caretaker typically manipulates the inserter 600 and the implant 501 when the application is a TLIF surgical procedure. FIG. 13A illustrates the starting position, in which the implant 501 is oriented with respect to the inserter 600 at about −10° relative to the longitudinal axis 602 of the inserter 600. The hook 620 and tab 630 both engage the facets 555 on the post 553 of the implant 501, thereby locking the implant 501 into a fixed position relative to the inserter 600. The caretaker can impact the implant 501, using a hammer or other suitable instrument, when the components of the system 700 are in the position shown in FIG. 13A.

Figure 13B:
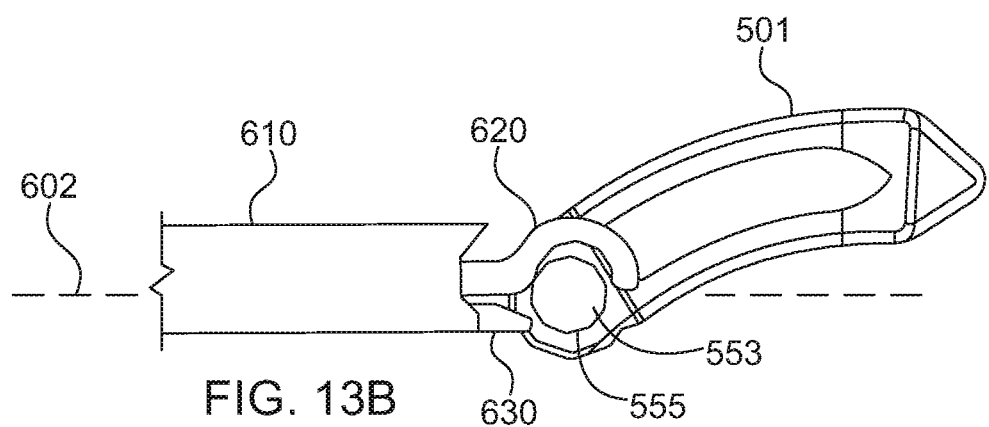

FIG. 13B illustrates the next step in the method, in which the caretaker, using the actuator 614, advances the hook 620 (and, therefore, the implant 501) away from the sleeve 610 so that the tab 630 no longer engages the facets 555 on the post 553 of the implant 501. Such disengagement frees the post 553 to rotate. Note that, although the tab 630 engages and disengages the facets 555 on the post 553 of the implant 501 throughout the steps in the method, the hook 620 continuously engages the facets 555 on the post 553 of the implant 501 throughout the method steps.

Figure 13C:
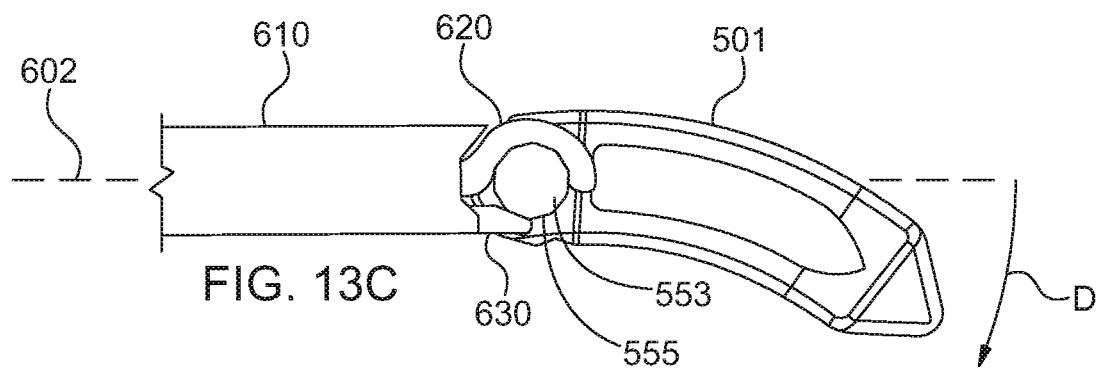

The caretaker next rotates the implant 501 by approximately 30-40° (and, more preferably, by about 33°) in the clockwise direction of arrow D, using the actuator 614, and retracts the hook 620 (and, therefore, the implant 501) into the sleeve 610 so that the tab 630 again engages the facets 555 on the post 553 of the implant 501. As illustrated in FIG. 13C, such engagement prevents further rotation of the post 553 and locks the implant 501 into a fixed position relative to the inserter 600. The implant 501 is now oriented with respect to the inserter 600 at about +20 to 30° (and, more preferably, by about +23°) relative to the longitudinal axis 602 of the inserter 600. The caretaker can again impact the implant 501, using a hammer or other suitable instrument, when the components of the system 700 are in the position shown in FIG. 13C.

Using the actuator 614, the caretaker can again advance the hook 620 (and, therefore, the implant 501) away from the sleeve 610 so that the tab 630 no longer engages the facets 555 on the post 553 of the implant 501. Such disengagement frees the post 553 to rotate. The caretaker next rotates the implant 501 by approximately 30-40° (and, more preferably, by about 33°) in the clockwise direction, using the actuator 614, and retracts the hook 620 (and, therefore, the implant 501) into the sleeve 610 so that the tab 630 again engages the facets 555 on the post 553 of the implant 501. As illustrated in FIG. 13D, such engagement prevents further rotation of the post 553 and locks the implant 501 into a fixed position relative to the inserter 600. The implant 501 is now oriented with respect to the inserter 600 at about +50 to 60° (and, more preferably, by about +57°) relative to the longitudinal axis 602 of the inserter 600. The caretaker can again impact the implant 501, using a hammer or other suitable instrument, when the components of the system 700 are in the position shown in FIG. 13D.

Finally, again using the actuator 614, the caretaker can advance the hook 620 (and, therefore, the implant 501) away from the sleeve 610 so that the tab 630 no longer engages the facets 555 on the post 553 of the implant 501. Such disengagement frees the post 553 to rotate. The caretaker next rotates the implant 501 by approximately 30-40° (and, more preferably, by about 33°) in the clockwise direction, using the actuator 614, and retracts the hook 620 (and, therefore, the implant 501) into the sleeve 610 so that the tab 630 again engages the facets 555 on the post 553 of the implant 501. As illustrated in FIG. 13E, such engagement prevents further rotation of the post 553 and locks the implant 501 into a fixed position relative to the inserter 600. The implant 501 is now oriented with respect to the inserter 600 at about +90° relative to the longitudinal axis 602 of the inserter 600. The caretaker can again impact the implant 501, using a hammer or other suitable instrument, when the components of the system 700 are in the position shown in FIG. 13E.

Figure 14:
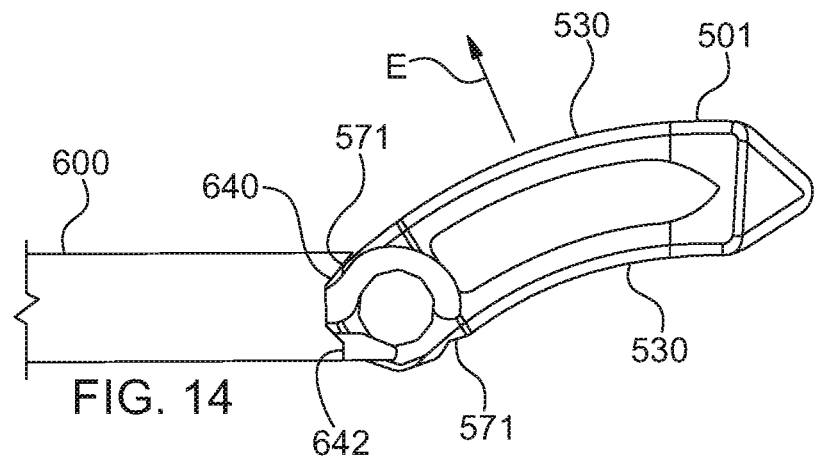
FIG. 14 illustrates the stops on the implant proximate one lateral side of the implant in contact with the first catch on the inserter when the implant is oriented with respect to the inserter at a specific angle relative to the longitudinal axis of the inserter.

As illustrated in FIG. 14 (or in FIGS. 13A and 13B), the stops 571 on the implant 501 proximate one lateral side 530 of the implant 501 contact the first catch 640 on the inserter 600 when the implant 501 is oriented with respect to the inserter 600 at about −10° relative to the longitudinal axis 602 of the inserter 600. Facilitated by the corresponding and preferably flat surfaces of the stops 571 and the first catch 640, such contact prevents over-rotation of the implant 501 relative to the inserter 600 in the direction of arrow E and beyond about −10°. Thus, such contact provides a safety function.

Figure 15:
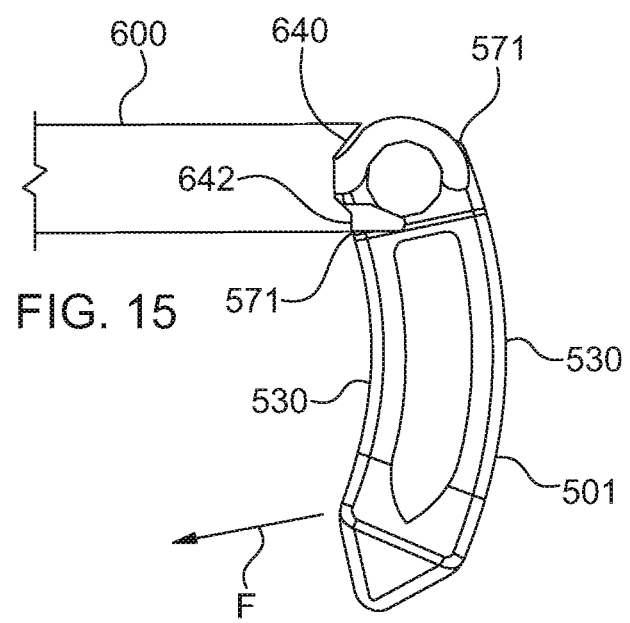
FIG. 15 illustrates the stops on the implant proximate the opposing lateral side of the implant in contact with the second catch on the inserter when the implant is oriented with respect to the inserter at another specific angle relative to the longitudinal axis of the inserter.

As illustrated in FIG. 15 (or in FIG. 13E), the stops 571 on the implant 501 proximate the opposing lateral side 530 of the implant 501 contact the second catch 642 on the inserter 600 when the implant 501 is oriented with respect to the inserter 600 at about +90° relative to the longitudinal axis 602 of the inserter 600. Facilitated by the corresponding and preferably flat surfaces of the stops 571 and the second catch 642, such contact prevents over-rotation of the implant 501 relative to the inserter 600 in the direction of arrow F and beyond about +90°. Thus, such contact provides a safety function.

In combination, the stops 571, the first catch 640, and the second catch 642 restrict rotation of the implant 501 relative to the inserter 600 within the range of about −10° to about +90°. Thus, over-articulation of the implant 501 relative to the inserter 600 is prevented. Of course, as an artisan would appreciate, the articulation range (about −10° to about +90° in the example) can be adjusted for a given application to other suitable ranges.

In summary, the system 700 for inserting the implant 1, 101, 101a, 201, 501, typically but not necessarily using a TLIF procedure, has two components: the implant 1, 101, 101a, 201, 501 and the inserter 600. The implant 1, 101, 101a, 201, 501 has a rigid, faceted post 553, typically a polygon such as a hexagon, that rotates; ribs 559 on the inserter engagement portion 551 of the implant 1, 101, 101a, 201, 501; and stops 571 to prevent over-rotating the implant 1, 101, 101a, 201, 501 relative to the inserter 600. The flat faces of the ribs 559 are adapted to receive impact (force) from a hammer or other instrument typically used by a caretaker to help position the implant 501 between vertebrae.

The inserter 600 has a sleeve 610 into and from which a robust, single hook 620 retracts and extends, and on which a tab 630 is disposed. The inserter 600 also has a pair of catches 640, 642. The static, rigid, manipulator tab 630 helps the caretaker to manipulate the implant 1, 101, 101a, 201, 501. The hook 620 and tab 630 combine to lock the post 553 into position and to release the post 553 so that the post 553 can rotate. The engagements between the hook 620 and the post 553 and between the tab 630 and the post 553 permit robust "turning" or rotation of the implant 1, 101, 101a, 201, 501 in situ. The stops 571 and catches 640, 642 define an articulation range (for example, about −10° to about +90°) for the implant 1, 101, 101a, 201, 501 relative to a longitudinal axis 602 of the inserter 600.

Having described the components of the system 700, an exemplary method by which a caretaker might use the system 700 follows. In operation, with specific reference to FIGS. 11A, 11B, 11C, 13A, 13B, 13C, 13D, and 13E, a spinal disc in need of repair or replacement is identified. The caretaker next performs at least a partial discectomy, preferably using a unilateral transforaminal approach. The caretaker then gauges the appropriate size of implant 501 to insert into the disc space (via measurement, a trial implant, or another technique known in the art) created by the discectomy. Bone graft material (not shown) is then optionally inserted into the internal cavity of the implant 501 defined by the vertical aperture 560.

The caretaker couples the implant 501 to the inserter 600, for example, by performing the three, general steps by which the inserter 600 engages the implant 501 illustrated in FIGS. 11A, 11B, and 11C and described above. Although other orientations are possible, the caretaker will typically orient the implant 501 to the inserter 600 as shown in FIG. 13A when coupling the implant 501 to the inserter 600. Next, the caretaker grasps the handle 612 of the inserter 600 and inserts the tapered nose 542 of the implant 501 into the transforaminal window created during the discectomy procedure until the tapered nose 542 enters the disc space and begins to distract the adjacent vertebral bodies.

The caretaker can deliver gentle hammer blows or other impaction forces to one or both of the proximal end 604 of the inserter 600 and the ribs 559 of the implant 501 to urge the implant 501 at least partially into the disc space. Toggling is prevented between the implant 501 and the inserter 600 during the delivery of impaction forces because the post 553 of the implant 501 is locked between the hook 620 and the tab 630 of the inserter 600. The engagement between the stops 571 of the implant 501 and the first catch 640 of the inserter 600 may also prevent toggling.

The caretaker manipulates the inserter 600 and the implant 501 using the steps illustrated in FIGS. 13A, 13B, 13C, 13D, and 13E and described above. Typically, as described above, three steps of sequential engagement, release, rotation, and re-engagement between the inserter 600 and the implant 501 are applied. These steps allow the caretaker to guide the implant 501 along a path to a desired final position within the disc space. The post 553 and, hence, the implant 501, rotates with respect to the inserter 600 within an articulation range defined by the stops 571, the first catch 640, and the second catch 642. Such rotation promotes turning of the implant 501 and guides the implant 501 along the path of insertion of the implant 501 as the tapered nose 542 progresses into the disc space.

The caretaker manipulates both the handle 612 and the actuator 614 of the inserter 600 until the optimum final positioning of the implant 501 is achieved with respect to the disc space. The insertion steps can be facilitated while viewing the position of the implant 501 if either markers are provided on the implant 501, which can be seen (for example) under fluoroscopic imaging, or X-rays are taken. Such markers, X-rays, or both can help the caretaker to determine the precise position of the implant 501 with respect to the disc space. Once the implant 501 is located in its final position, the caretaker releases the implant 501 from the inserter 600 by manipulating the handle 612 and the actuator 614 so that neither the hook 620 nor the tab 630 engage the post 553. The compression forces between the vertebral endplates and the top surface 510 and the bottom surface 520 of the implant 501 maintain the implant 501 in place as the caretaker removes the inserter 600 from the disc space and from the body of the patient.

Imaging or X-rays can ascertain for the caretaker that the implant 501 is located precisely and correctly in its final position. The vertical aperture 560 and transverse aperture 570 can be viewed using lateral and/or frontal X-rays, for example, to confirm the appropriate position of the implant 501 within the disc space. Throughout the entirety of the insertion process, the angle and position of the inserter 600 with respect to the disc space can be maintained substantially constant; the actions performed by the caretaker to articulate the implant 501 do not require movement of the inserter 600.

The spinal implant 501 and the associated inserter 600, and the related method of using the system 700, improve the ease with which the implant 501 may be manipulated during insertion or once within the disc space. The implant 501, inserter 600, and method keep the insertion width of the system 700 smaller and enable the caretaker to manipulate the implant 501 within the disc space, in situ, without passing multiple instruments by the exposed nerve roots. The system 700 avoids the need for a large incision and subsequent trauma to the spine, as well as reduces the risk of damaging the nerve root with multiple passes of instrumentation.

Although illustrated and described above with reference to certain specific embodiments and examples, the present invention is nevertheless not intended to be limited to the details shown. Rather, various modifications may be made in the details within the scope and range of equivalents of the claims and without departing from the spirit of the invention. It is expressly intended, for example, that all ranges broadly recited in this document include within their scope all narrower ranges which fall within the broader ranges. It is also expressly intended that the steps of the methods of using the various devices disclosed above are not restricted to any particular order.

What is claimed:

1. A system for use during surgical procedures, the system comprising:
   an implant having a faceted post that rotates, ribs adapted to receive impact from an instrument to help position the implant, and stops; and
   an inserter having a sleeve, into and from which a hook retracts and extends and to which a tab is fixedly connected, and a pair of catches,
   wherein the hook and tab combine to lock the post into position and to release the post so that the post can rotate, a direct engagement between the hook and the post and between the tab and the post permit rotation of the implant in situ, and the stops and catches define an articulation range for the implant relative to a longitudinal axis of the inserter.

2. The system of claim 1, wherein the post is recessed within a slot of the implant.

3. The system of claim 2, wherein the slot forms a step in the implant.

4. The system of claim 1, wherein the post is configured to rotate about a vertical axis relative to the implant.

5. The system of claim 1, where the ribs are separated by a series of columns.

6. The system of claim 5, wherein each of the ribs and columns has a flat surface, and wherein a junction between the rib and columns is angled.

7. The system of claim 1, wherein the inserter has an actuator configured to manipulate the hook.

8. The system of claim 1, wherein the hook has an inner surface shaped to correspond geometrically with the faceted post.

9. The system of claim 1, wherein the tab has an inner surface shaped to correspond geometrically with the faceted post.

10. The system of claim 1, wherein the implant includes a body having a top surface, a bottom surface, opposing lateral sides, and opposing anterior and posterior sides.

11. The system of claim 10, wherein the post, ribs, and stops are located on the posterior side of the implant.

12. A system for use during surgical procedures, the system comprising:
   an implant having a faceted post that rotates, ribs adapted to receive impact from an instrument to help position the implant, and stops; and
   an inserter having a sleeve, into and from which a hook retracts and extends and to which a tab is fixedly connected, an actuator to manipulate the hook, and a pair of catches, wherein the hook has an inner surface shaped to correspond geometrically with the faceted post,
wherein the tab has an inner surface shaped to correspond geometrically with the faceted post, and
wherein the hook and tab combine to lock the post into position and to release the post so that the post can rotate, the engagements between the hook and the post and between the tab and the post permit rotation of the implant in situ, and the stops and catches define an articulation range for the implant relative to a longitudinal axis of the inserter.

13. The system of claim 12, wherein the post is recessed within a slot of the implant.

14. The system of claim 13, wherein the slot forms a step in the implant.

15. The system of claim 12, wherein the post is configured to rotate about a vertical axis relative to the implant.

16. The system of claim 12, where the ribs are separated by a series of columns.

17. The system of claim 16, wherein each of the ribs and columns has a flat surface, and wherein a junction between the rib and columns is angled.

18. A method for using a system including an implant and an inserter during a surgical procedure, after a spinal disc in need of repair or replacement is identified, at least a partial discectomy is performed to create a disc space, and the appropriate size of implant is gauged and selected for the disc space, the method comprising the steps of:
(a) coupling the implant to the inserter by manipulating an actuator of the inserter to extend a hook away from a sleeve and, using a handle of the inserter, manipulating the sleeve so that the hook engages a post of the implant, manipulating the actuator to retract the hook into the sleeve and translate the hook relative to a tab of the inserter until the post of the implant engages the tab, with full engagement between the hook and the post and between the tab and the post locking the post into the hook and the tab, preventing rotation of the post;
(b) grasping the handle of the inserter and inserting a tapered nose of the implant into the disc space created during the discectomy procedure until the tapered nose enters the disc space and begins to distract the adjacent vertebral bodies;
(c) optionally delivering impaction forces to one or both of a proximal end of the inserter and ribs of the implant to urge the implant at least partially into the disc space;
(d) manipulating the inserter and the implant sequentially to engage, release the tab from the post of, rotate, and re-engage the tab with the post of the implant to guide the implant along a path to a desired final position within the disc space;
(e) releasing the implant from the inserter by manipulating the handle and the actuator so that neither the hook nor the tab engage the post; and
(f) removing the inserter from the disc space.

19. The method according to claim 18, the method further comprises the step of preventing toggling between the implant and the inserter.

20. The method according to claim 18, the method further comprising the step of preventing over-rotation of the implant relative to the inserter.

* * * * *